US007252936B2

(12) United States Patent
De Beenhouwer et al.

(10) Patent No.: US 7,252,936 B2
(45) Date of Patent: Aug. 7, 2007

(54) METHOD FOR THE DETECTION OF THE ANTIBIOTIC RESISTANCE SPECTRUM OF MYCOBACTERIUM SPECIES

(75) Inventors: Hans De Beenhouwer, Lennik (BE); Françoise Portaels, Brussels (BE); Lieve Machtelinckx, Gullegem (BE); Geert Jannes, Kessel-Lo (BE); Rudi Rossau, Ekeren (BE)

(73) Assignee: Innogenetics N.V., Ghent (BE)

( * ) Notice: Subject to any disclaimer, the term of this patent is extended or adjusted under 35 U.S.C. 154(b) by 574 days.

(21) Appl. No.: 10/339,604

(22) Filed: Jan. 10, 2003

(65) Prior Publication Data

US 2003/0152982 A1 Aug. 14, 2003

Related U.S. Application Data

(60) Division of application No. 09/722,319, filed on Nov. 28, 2000, now Pat. No. 6,632,607, which is a continuation of application No. 08/750,088, filed as application No. PCT/EP95/02230 on Jun. 9, 1995, now Pat. No. 6,329,138.

(30) Foreign Application Priority Data

Jun. 9, 1994 (EP) .................................. 94870093
Dec. 14, 1995 (WO) .................................. 95/33851

(51) Int. Cl.
C12Q 1/68 (2006.01)
C12P 19/34 (2006.01)
C07H 21/04 (2006.01)
C07H 21/00 (2006.01)

(52) U.S. Cl. .................... 435/6; 435/91.1; 435/91.2; 536/22.1; 536/24.3; 536/25.3

(58) Field of Classification Search .................... 435/6, 435/91.1, 91.2; 536/22.1, 24.3, 25.3
See application file for complete search history.

(56) References Cited

U.S. PATENT DOCUMENTS

| 5,633,131 A | 5/1997 | Heym et al. .................... 435/6 |
| 5,643,723 A | 7/1997 | Persing et al. .................. 435/6 |
| 5,851,763 A | 12/1998 | Heym et al. .................... 435/6 |

FOREIGN PATENT DOCUMENTS

| EP | 0 639 229 B1 | 2/1995 |
| WO | WO 88/03957 | 6/1988 |
| WO | WO 93/22454 | 11/1993 |
| WO | WO 95/33074 | 12/1995 |
| WO | WO 95/33851 | 12/1995 |

OTHER PUBLICATIONS

Banerjee, A. et al., "*inhA*, a Gene Encoding a Target for Isoniazid and Ethionamide in *Mycobacterium tuberculosis*," *Science* 263:227-230, American Association for the Advancement of Science (Jan. 1994).

Bej, A.K. et al., "Multiplex PCR amplification and immobilized capture probes for detection of bacterial pathogens and indicators in water," *Mol. Cell. Probes* 4:353-365, Academic Press Ltd (Oct. 1990).

Canetti, G. et al., "Mycobacteria: Laboratory Methods for Testing Drug Sensitivity and Resistance," *Bull W.H.O.* 29:565-578, World Health Organization (1963).

Clarridge III, J.E. et al., "Large-Scale Use of Polymerase Chain Reaction for Detection of *Mycobacterium tuberculosis* in a Routine Mycobacterium Laboratory," *J. Clin. Microbiol.* 31:2049-2056, American Society for Microbiology (Aug. 1993).

Culliton, B.J., "Drug-resistant TB may bring epidemic," *Nature* 356:473, Macmillan Publishers Ltd (Apr. 1992).

De Beenhouwer, H. et al., "Easy Detection Method ofr Rifampicin Resistance of *M. tuberculosis* Directly in Clinical Samples," *Tubercle and Lung Dis.* 75(Supp. 1):13, Abstract No. 44, Churchill Livingstone (Jun. 1994).

De Beenhouwer, H. et al., "Rapid detection of rifampicin resistance in sputum and biopsy specimens from tuberculosis patients by PCR and line probe assay," *Tubercle & Lung Dis.* 76:425-430, Pearson Professional Ltd (Oct. 1995).

Donnabella, V. et al., "Isolation of the Gene for the β Subunit of RNA Polymerase from Rifampicin-resistant *Mycobacterium tuberculosis* and Identification of New Mutations," *Am. J. Respir. Cell. Mol. Biol.* 11:639-643, American Thoracic Society (Dec. 1994).

Douglass, J. and Steyn, L.M., "A Ribosomal Gene Mutation in Streptomycin-Resistant *Mycobacterium tuberculosis* Isolates," *J. Infect. Dis* 167:1505-1506, University of Chicago Press (Jun. 1993).

Felmlee, T.A. et al., "Genotypic Detection of *Mycobacterium tuberculosis* Rifampin Resistance: Comparison of Single-Strand Conformation Polymorphism and Dideoxy Fingerprinting," *J. Clin. Microbiol.* 33:1617-1623, American Society for Microbiology (Jun. 1995).

(Continued)

*Primary Examiner*—Kenneth R. Horlick
*Assistant Examiner*—Joyce Tung
(74) *Attorney, Agent, or Firm*—Sterne, Kessler, Goldstein & Fox PLLC

(57) ABSTRACT

Method for the detection of the antibiotic resistance spectrum of *Mycobacterium* species present in a sample, possibly coupled to the identification of the *Micobacterium* species involved, comprising the steps of: (i) if need be releasing, isolating or concentrating the polynucleic acids present in the sample; (ii) if need be amplifying the relevant part of the antibiotic resistance genes present in said sample with at least one suitable primer pair; (iii) hybridizing the polynucleic acids of step (i) or (ii) with at least one of the rpoB gene probes, as specified in table 2, under the appropriate hybridization and wash conditions; (iv) detecting the hybrids formed in step (iii); (v) inferring the *Mycobacterium* antibiotic resistance spectrum, and possibly the *Mycobacterium* species involved from the differential hybridization signal(s) obtained in step (iv).

7 Claims, 11 Drawing Sheets

OTHER PUBLICATIONS

Pinken, M. et al., "Molecular basis of streptomycin resistance in *Mycobacterium tuberculosis*: alterations of the ribosomal protein S12 gene and point mutations within a functional 16S ribosomal RNA pseudoknot," *Mol. Microbiol. 9*:1239-1246, Blackwell Scientific Publications (Sep. 1993).

Guerrero, C. et al., "Evaluation of the *rpoB* gene in rifampicin-susceptible and—resistant *Mycobacterium avium* and *Mycobacterium intracellulare*," *J. Antimicrob. Chemother. 33*:661-663, British Society for Antimicrobial Chemotherapy (Mar. 1994).

Heifets, L., "Qualitative and Quantitative Drug-susceptibility Tests in Mycobacteriology," *Am. Rev. Resp. Dis 137*:1217-1222, American Thoracic Society (May 1988).

Honore, N. and Cole,S.T., "Molecular Basis of Rifampin Resistance in *Mycobacterium leprae*," *Antimicrob. Agents Chemother. 37*:414-418, American Society for Microbiology (Mar. 1993).

Hunt, J.M. et al., "Detection of a Genetic Locus Encoding Resistance to Rifampin in Mycobacterial Cultures and in Clinical Specimens," *Diagn. Microbiol. Infect. Dis. 18*:219-227, Elsevier Science Inc. (Apr. 1994).

Kapur, V. et al., "Characterization by Automated DNA Sequencing of Mutations in the Gene (*rpoB*) Encoding the RNA Polymerase β Subunit in Rifampin-Resistant *Mycobacterium tuberculosis* Strains from New York City and Texas," *J. Clin. Microbiol. 32*:1095-1098, American Society for Microbiology (Apr. 1994).

Middlebrook, G., "Isoniazid-Resistance and Catalase Activity of *Tubercle bacilli*," *Am. Rev. Tuberculosis 69*:471-472, National Tuberculosis Association (Mar. 1954).

Middlebrook, G. et al., "Studies on Isoniazid and *Tubercle bacilli*: III. The Isolation, Drug-Susceptibility, and Catalase-Testing of *Tubercle bacilli* from Isoniazid-Treated Patients," *Am. Rev. Tuberculosis 70*:852-872, National Tuberculosis Association (Nov. 1954).

Nair, J. et al., "The rpsL gene and streptomycin resistance in single and multiple drug-resistant strains of *Mycobacterium tuberculosis*," *Mol. Microbiol. 10*:521-527, Blackwell Scientific Publications (Nov. 1993).

Saiki, R.K. et al., "Genetic analysis of amplified DNA with immobilized sequence-specific oligonucleotide probes," *Proc. Natl. Acad. Sci. USA 86*:6230-6234, National Academy of Sciences of the USA (Aug. 1989).

Stoeckle, M.Y. et al., "Catalase-Peroxidase Gene Sequences in Isoniazid-Sensitive and -Resistant Strains of *Mycobacterium tuberculosis* from New York City," *J. Infect. Dis. 168*:1063-1065, University of Chicago Press (Oct. 1993).

Stuyver, L. et al., "Typing of hepatitis C virus isolates and characterization of new subtypes using a line probe assay," *J. Gen. Virol. 74*:1093-1102, Society for General Microbiology (Jun. 1993).

Telenti, A. et al., "Detection of rifampicin-resistant mutations in *Mycobacterium tuberculosis*," *Lancet 341*:647-650, Williams & Wilkins (Mar. 1993).

Telenti, A. et al., "Direct, Automated Detection of Rifampin-Resistant *Mycobacterium tuberculosis* by Polymerase Chain Reaction and Single-Strand Conformational Polymorphism Analysis," *Antimicrob. Agents Chemother. 37*:2054-2058, American Society for Microbiology (Oct. 1993).

van Belkum, A. et al., "Non-Isotopic Labeling of DNA by Newly Developed Hapten-Containing Platinum Compounds," *BioTechniques 16*:148-152, Eaton Publishing Co. (1994).

Whelen, A.C. et al., "Rapid and Specific PCR-based Detection of Drug-resistant and -sensitive *Mycobacterium tuberculosis* (MTB) by Amplification of the RNA polymerase Gene *rpoB*," *Abstracts of the 94th General Meeting of the American Society for Microbiology*:196, Abstract U-134, American Society for Microbiology (1994).

Whelen, A.C. et al., "Direct Genotypic Detection of *Mycobacterium tuberculosis*, Rifampin Resistance in Clinical Specimens by Using Single-Tube Heminested PCR," *J. Clin. Microbiol. 33*:556-561, American Society for Microbiology (Mar. 1995).

Williams, D.L. et al., "Characterization of Rifampin Resistance in Pathogenic Mycobacteria," *Antimicrobial Agents & Chemother. 38*:2380-2386, American Society for Microbiology (Oct. 1994).

Youatt, J., "A Review of the Action of Isoniazid," *Am. Rev. Resp. Dis 99*:729-749, American Thoracic Society (May 1969).

Zhang, Y. et al., "The catalase-peroxidase gene and isoniazid resistance of *Mycobacterium tuberculosis*," *Nature 358*:591-593, Macmillan Publishers Ltd (Aug. 1992).

International Search Report for PCT/EP95/02230, mailed Jan. 9, 1996.

Stratagene Catalog, Stratagene p. 39 (1988).

ITG 9003

GATCCGGGTC GGCATGTCGC GGATGGAGCG GGTGGTCCGG GAGCGGATGA CCACCCAGGA CGTGGAGGCG
ATCACACCGC AGACGTTGAT CAACATCCGG CCGGTGGTCG CCGCGATCAA GGAGTTCTTC GGCACCAGCC
AGCTGAGCCA ATTCATGGAC CAGAACAACC CGCTGTCGGG GTTGACCTGC AAGCGCCGAC TGTCGGCGCT
GGGGCCCGGN GGTCTGTCAC CAGAGCGTGC CGGGCTGGAG GTCCGCGACG TGCACCCGTC GCACTACGGN
CGGATGTGCC CTATCGAAAC CCCTGAGGGG GCCAACATCG NTCTTTATC

FIG. 2

|  | 8872 | 9081 |
|---|---|---|
| control line | — | — |
| probe S44 { 2.4 | | |
| 1.2 | | |
| 0.6 | | |
| probe S4444 { 2.4 | ■ | ■ |
| 1.2 | ■ | ■ |
| 0.6 | ■ | ■ |
| pmol | | |

Fig. 3

|   A   |   B   |
|-------|-------|
| C     | C     |
| MT-POL-1 | MT-POL-1 |
| S1    | S1    |
| S2    | S2    |
| R2    | S33   |
| S33   | S4444 |
| S44   | S55   |
| R44A  | R2    |
| R44B  | R44A  |
| S55   | R44B  |
| R55   | R55   |

Fig. 4

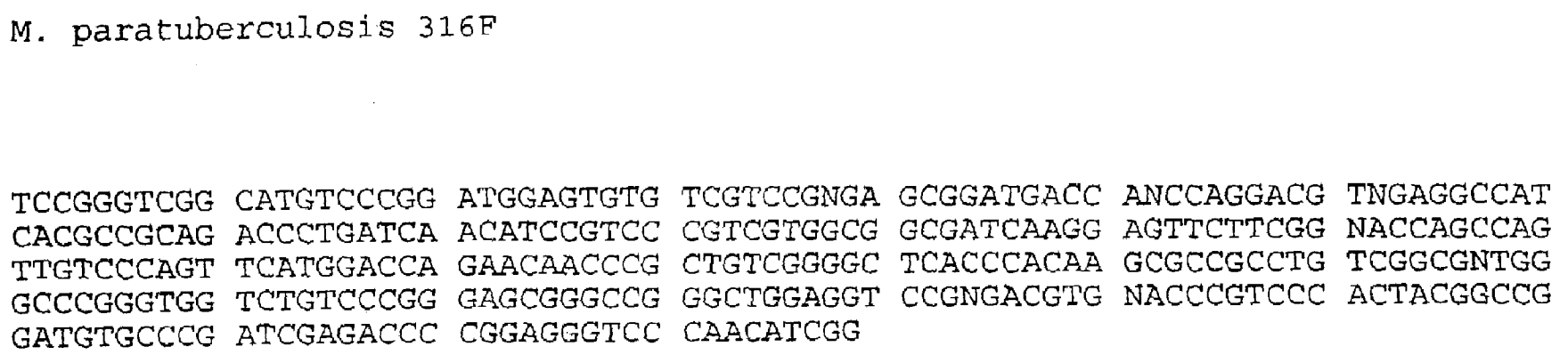

M. paratuberculosis 316F

```
TCCGGGTCGG CATGTCCCGG ATGGAGTGTG TCGTCCGNGA GCGGATGACC ANCCAGGACG TNGAGGCCAT
CACGCCGCAG ACCCTGATCA ACATCCGTCC CGTCGTGGCG GCGATCAAGG AGTTCTTCGG NACCAGCCAG
TTGTCCCAGT TCATGGACCA GAACAACCCG CTGTCGGGGC TCACCCACAA GCGCCGCCTG TCGGCGNTGG
GCCCGGGTGG TCTGTCCCGG GAGCGGGCCG GGCTGGAGGT CCGNGACGTG NACCCGTCCC ACTACGGCCG
GATGTGCCCG ATCGAGACCC CGGAGGGTCC CAACATCGG
```

FIG. 5

M. avium ITG 5887

```
GGATGGAGCG CTCCGTCCGC GAGCGGGATGA CCACCCAGGA CGTCGAGGCC ATCACGCCGC AGACCCTGAT
CAACATCCGT CCAGTCGTGG CGGCGATCAA GGAGTTCTTC GGCACCAGCC AGCTGTCCCA GTTCATGGAC
CAGAACAACC CGCTGTCGGG GCTCACCCAC AAGCGCCGCC TGTCGGCGCT GGGCCCGGGT GGTCTGTCCC
GGGAGCGGGC CGGGCTGGAG GTCCGCGACG TGCACCCGTC CCACTACGGC CGGATGTGCC CGATCGAGAC
CCCGGAGGGT CCCAACATCG GTCTGATCGG CTCGCTGTCG GTGT
```

FIG. 6

M. scrofulaceum ITG 4979

CGGGTCGGCA TGTCCCGCAT GGAGCGGGTC GTCCGCGAGC GGATGACCAC GCAGGACGTC GAGGCGATCA
CGCCGGCAGAC CCTGATCAAC ATCCGGCCGG TCGTGGCCGC GATCAAGGAG TTCTTCGGCA CCAGCCAGCT
CTCGCCAGTTC ATGGACCAGA ACAACCCGNT GTCGGGCCTG ACCCACAAGC GCCGCCTGTC GGTGCTGGGC
CCGGTTGGTC TGTCCCGCGA GCGGGCCGGG TTGGAGGTCC GGAG

FIG. 7

M. kansasii ITG 4987

GGATGGAACG GGTGGTCCGG GNNNNGGATG ACCACTCAGG ACGTCGAGGC GATCACGCCG
AGACACTGAT CAACATCCGC CCGGTGGTCG CCGCCATCAA GGAGTTCTTC GGCACCAGCC
AGCTCTCCCA GTTCATGGAC CAGAACAACC CGCTGTCGGG CCTCACCCAC AAGCGCGGC
TTTCGGCGCT GGGGCCGGGC GGTCTGTCCC GGGAGCGTGC CGGGCTGGAG GTCCGCGATG
CTC

FIG. 8

MAC strain ITG 926

GGCATTTNAC GGATGGAACG CGTGGTCCGC GANCGGATGA CCACGCAGGA CGTCGAGGCC ATCACGCCGC
AGACCCTGAT CAACATCCGG CCGGTCGTCG CCGCGATCAA GGAGTTCTTC GGGACCAGCC AGCTGTCGCA
GTTCATGGAC CAGAACAACC CGCTGTCGGG TCTGACCCAC AAGCGTCGCC TGTCGGCGCT GGGTCCCGGC
GGTCTGTCCC GTGAGCGC

FIG. 11

```
                          SEQUENCE LISTING

<160> NUMBER OF SEQ ID NOS: 73

<210> SEQ ID NO 1
<211> LENGTH: 22
<212> TYPE: DNA
<213> ORGANISM: Artificial Sequence
<220> FEATURE:
<223> OTHER INFORMATION: Probe

<400> SEQUENCE: 1
cagccagctg agccaattca tg                                                22

<210> SEQ ID NO 2
<211> LENGTH: 21
<212> TYPE: DNA
<213> ORGANISM: Artificial Sequence
<220> FEATURE:
<223> OTHER INFORMATION: Probe

<400> SEQUENCE: 2
cagccagctg agccaattca t                                                 21

<210> SEQ ID NO 3
<211> LENGTH: 22
<212> TYPE: DNA
<213> ORGANISM: Mycobacterium sp.

<400> SEQUENCE: 3
ttcatggacc agaacaaccc gc                                                22

<210> SEQ ID NO 4
<211> LENGTH: 19
<212> TYPE: DNA
<213> ORGANISM: Artificial Sequence
<220> FEATURE:
<223> OTHER INFORMATION: Probe

<400> SEQUENCE: 4
```

-continued aacccgctgt cggggttga                    19

<210> SEQ ID NO 5
<211> LENGTH: 21
<212> TYPE: DNA
<213> ORGANISM: Artificial Sequence
<220> FEATURE:
<223> OTHER INFORMATION: Probe

<400> SEQUENCE: 5
aacccgctgt cggggttgac c                 21

<210> SEQ ID NO 6
<211> LENGTH: 19
<212> TYPE: DNA
<213> ORGANISM: Artificial Sequence
<220> FEATURE:
<223> OTHER INFORMATION: Probe

<400> SEQUENCE: 6
gttgacccac aagcgccga                    19

<210> SEQ ID NO 7
<211> LENGTH: 20
<212> TYPE: DNA
<213> ORGANISM: Artificial Sequence
<220> FEATURE:
<223> OTHER INFORMATION: Probe

<400> SEQUENCE: 7
ggttgaccca caagcgccga                   20

<210> SEQ ID NO 8
<211> LENGTH: 23
<212> TYPE: DNA
<213> ORGANISM: Artificial Sequence
<220> FEATURE:
<223> OTHER INFORMATION: Probe

<400> SEQUENCE: 8
ttgacccaca agcgccgact gtc               23

<210> SEQ ID NO 9
<211> LENGTH: 17
<212> TYPE: DNA
<213> ORGANISM: Artificial Sequence
<220> FEATURE:
<223> OTHER INFORMATION: Probe

<400> SEQUENCE: 9
gactgtcggc gctgggg                      17

<210> SEQ ID NO 10
<211> LENGTH: 19
<212> TYPE: DNA
<213> ORGANISM: Artificial Sequence
<220> FEATURE:
<223> OTHER INFORMATION: Probe

<400> SEQUENCE: 10
cgactgtcgg cgctggggc                    19

<210> SEQ ID NO 11
<211> LENGTH: 22
<212> TYPE: DNA
<213> ORGANISM: Artificial Sequence

```
<220> FEATURE:
<223> OTHER INFORMATION: Probe

<400> SEQUENCE: 11
tgagccaatt catggaccag aa                                              22

<210> SEQ ID NO 12
<211> LENGTH: 22
<212> TYPE: DNA
<213> ORGANISM: Artificial Sequence
<220> FEATURE:
<223> OTHER INFORMATION: Probe

<400> SEQUENCE: 12
ctgagccaat tcatggacca ga                                              22

<210> SEQ ID NO 13
<211> LENGTH: 19
<212> TYPE: DNA
<213> ORGANISM: Artificial Sequence
<220> FEATURE:
<223> OTHER INFORMATION: Probe

<400> SEQUENCE: 13
ccacaagcgt cgactgtcg                                                  19

<210> SEQ ID NO 14
<211> LENGTH: 23
<212> TYPE: DNA
<213> ORGANISM: Artificial Sequence
<220> FEATURE:
<223> OTHER INFORMATION: Probe

<400> SEQUENCE: 14
aattcatggt ccagaacaac ccg                                             23

<210> SEQ ID NO 15
<211> LENGTH: 20
<212> TYPE: DNA
<213> ORGANISM: Artificial Sequence
<220> FEATURE:
<223> OTHER INFORMATION: Probe

<400> SEQUENCE: 15
ggttgaccta caagcgccga                                                 20

<210> SEQ ID NO 16
<211> LENGTH: 21
<212> TYPE: DNA
<213> ORGANISM: Artificial Sequence
<220> FEATURE:
<223> OTHER INFORMATION: Probe

<400> SEQUENCE: 16
gggttgacct acaagcgccg a                                               21

<210> SEQ ID NO 17
<211> LENGTH: 23
<212> TYPE: DNA
<213> ORGANISM: Artificial Sequence
<220> FEATURE:
<223> OTHER INFORMATION: Probe

<400> SEQUENCE: 17
ttgacctaca agcgccgact gtc                                             23
```

```
<210> SEQ ID NO 18
<211> LENGTH: 19
<212> TYPE: DNA
<213> ORGANISM: Artificial Sequence
<220> FEATURE:
<223> OTHER INFORMATION: Probe

<400> SEQUENCE: 18
gttgaccgac aagcgccga                                                  19

<210> SEQ ID NO 19
<211> LENGTH: 20
<212> TYPE: DNA
<213> ORGANISM: Artificial Sequence
<220> FEATURE:
<223> OTHER INFORMATION: Probe

<400> SEQUENCE: 19
ggttgaccga caagcgccga                                                 20

<210> SEQ ID NO 20
<211> LENGTH: 23
<212> TYPE: DNA
<213> ORGANISM: Artificial Sequence
<220> FEATURE:
<223> OTHER INFORMATION: Probe

<400> SEQUENCE: 20
ttgaccgaca agcgccgact gtc                                             23

<210> SEQ ID NO 21
<211> LENGTH: 18
<212> TYPE: DNA
<213> ORGANISM: Artificial Sequence
<220> FEATURE:
<223> OTHER INFORMATION: Probe

<400> SEQUENCE: 21
cgactgttgg cgctggggg                                                  18

<210> SEQ ID NO 22
<211> LENGTH: 19
<212> TYPE: DNA
<213> ORGANISM: Artificial Sequence
<220> FEATURE:
<223> OTHER INFORMATION: Probe

<400> SEQUENCE: 22
cgactgttgg cgctggggc                                                  19

<210> SEQ ID NO 23
<211> LENGTH: 21
<212> TYPE: DNA
<213> ORGANISM: Artificial Sequence
<220> FEATURE:
<223> OTHER INFORMATION: Probe

<400> SEQUENCE: 23
ggacgtggag gcgatcacac c                                               21

<210> SEQ ID NO 24
<211> LENGTH: 23
<212> TYPE: DNA
<213> ORGANISM: Artificial Sequence
<220> FEATURE:
<223> OTHER INFORMATION: Probe
```

```
<400> SEQUENCE: 24
cgatcacacc gcagacgttg atc                                             23

<210> SEQ ID NO 25
<211> LENGTH: 18
<212> TYPE: DNA
<213> ORGANISM: Artificial Sequence
<220> FEATURE:
<223> OTHER INFORMATION: Probe

<400> SEQUENCE: 25
catccggccg gtggtcgc                                                   18

<210> SEQ ID NO 26
<211> LENGTH: 17
<212> TYPE: DNA
<213> ORGANISM: Artificial Sequence
<220> FEATURE:
<223> OTHER INFORMATION: Probe

<400> SEQUENCE: 26
ctggggcccg gcggtct                                                    17

<210> SEQ ID NO 27
<211> LENGTH: 20
<212> TYPE: DNA
<213> ORGANISM: Artificial Sequence
<220> FEATURE:
<223> OTHER INFORMATION: Probe

<400> SEQUENCE: 27
cggtctgtca cgtgagcgtg                                                 20

<210> SEQ ID NO 28
<211> LENGTH: 18
<212> TYPE: DNA
<213> ORGANISM: Artificial Sequence
<220> FEATURE:
<223> OTHER INFORMATION: Probe

<400> SEQUENCE: 28
catccgtccc gtcgtggc                                                   18

<210> SEQ ID NO 29
<211> LENGTH: 19
<212> TYPE: DNA
<213> ORGANISM: Artificial Sequence
<220> FEATURE:
<223> OTHER INFORMATION: Probe

<400> SEQUENCE: 29
catccgtcca gtcgtggcg                                                  19

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30
gagaattcgg tcggcgagct gatcc                                           25

<210> SEQ ID NO 31
```

```
<211> LENGTH: 20
<212> TYPE: DNA
<213> ORGANISM: Artificial Sequence
<220> FEATURE:
<223> OTHER INFORMATION: Primer

<400> SEQUENCE: 31
ggtcggcatg tcgcggatgg                                              20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
gcacgtcgcg gacctccagc                                              20

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33
cgaagcttga cccgcgctac acc                                          23

<210> SEQ ID NO 34
<211> LENGTH: 329
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (220)..(220)
<223> OTHER INFORMATION: n can be any nucleotide
<220> FEATURE:
<221> NAME/KEY: misc_feature
<222> LOCATION: (280)..(280)
<223> OTHER INFORMATION: n can be any nucleotide
<220> FEATURE:
<221> NAME/KEY: misc_feature
<222> LOCATION: (321)..(321)
<223> OTHER INFORMATION: n can be any nucleotide

<400> SEQUENCE: 34
gatccgggtc ggcatgtcgc ggatggagcg ggtggtccgg gagcggatga ccacccagga    60
cgtggaggcg atcacaccgc agacgttgat caacatccgg ccgtggtcg ccgcgatcaa    120 ggagttcttc ggcaccagcc agctgagcca attcatggac cagaacaacc cgctgtcggg   180
gttgacctgc aagcgccgac tgtcggcgct ggggcccggn ggtctgtcac gtgagcgtgc   240
cgggctggag gtccgcgacg tgcacccgtc gcactacggn cggatgtgcc ctatcgaaac   300
ccctgagggg gccaacatcg ntctttatc                                    329

<210> SEQ ID NO 35
<211> LENGTH: 319
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (38)..(38)
<223> OTHER INFORMATION: n can be any nucleotide
```

```
<220> FEATURE:
<221> NAME/KEY: misc_feature
<222> LOCATION: (52)..(52)
<223> OTHER INFORMATION: n can be any nucleotide
<220> FEATURE:
<221> NAME/KEY: misc_feature
<222> LOCATION: (62)..(62)
<223> OTHER INFORMATION: n can be any nucleotide
<220> FEATURE:
<221> NAME/KEY: misc_feature
<222> LOCATION: (131)..(131)
<223> OTHER INFORMATION: n can be any nucleotide
<220> FEATURE:
<221> NAME/KEY: misc_feature
<222> LOCATION: (207)..(207)
<223> OTHER INFORMATION: n can be any nucleotide
<220> FEATURE:
<221> NAME/KEY: misc_feature
<222> LOCATION: (254)..(254)
<223> OTHER INFORMATION: n can be any nucleotide
<220> FEATURE:
<221> NAME/KEY: misc_feature
<222> LOCATION: (261)..(261)
<223> OTHER INFORMATION: n can be any nucleotide

<400> SEQUENCE: 35
tccgggtcgg catgtcccgg atggagtgtg tcgtccgnga gcggatgacc anccaggacg      60
tngaggccat cacgccgcag accctgatca acatccgtcc cgtcgtggcg gcgatcaagg     120
agttcttcgg naccagccag ttgtcccagt tcatggacca gaacaacccg ctgtcggggc     180
tcacccacaa gcgccgcctg tcggcgntgg gcccgggtgg tctgtcccgg gagcgggccg     240
ggctggaggt ccgngacgtg nacccgtccc actacggccg gatgtgcccg atcgagaccc     300
cggagggtcc caacatcgg                                                  319

<210> SEQ ID NO 36
<211> LENGTH: 324
<212> TYPE: DNA
<213> ORGANISM: Artificial Sequence
<220> FEATURE:
<223> OTHER INFORMATION: Probe

<400> SEQUENCE: 36
ggatggagcg ctccgtccgc gagcggatga ccacccagga cgtcgaggcc atcacgccgc      60
agaccctgat caacatccgt ccagtcgtgg cggcgatcaa ggagttcttc ggcaccagcc     120
agctgtccca gttcatggac cagaacaacc cgctgtcggg gctcacccac aagcgccgcc     180
tgtcggcgct gggcccgggt ggtctgtccc gggagcgggc cggctggag gtccgcgacg      240 tgcacccgtc ccactacggc cggatgtgcc cgatcgagac cccggagggt cccaacatcg     300
gtctgatcgg ctcgctgtcg gtgt                                            324

<210> SEQ ID NO 37
<211> LENGTH: 254
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (169)..(169)
<223> OTHER INFORMATION: n can be any nucleotide

<400> SEQUENCE: 37
cgggtcggca tgtcccgcat ggagcgggtc gtccgcgagc ggatgaccac gcaggacgtc      60
gaggcgatca cgccgcagac cctgatcaac atccggccgg tcgtggccgc gatcaaggag     120
```

```
ttcttcggca ccagccagct ctcgcagttc atggaccaga acaacccgnt gtcgggcctg    180
acccacaagc gccgcctgtc ggtgctgggc ccggttggtc tgtcccgcga gcgggccggg    240
ttggaggtcc ggag                                                      254
```

<210> SEQ ID NO 38
<211> LENGTH: 16
<212> TYPE: DNA
<213> ORGANISM: Artificial Sequence
<220> FEATURE:
<223> OTHER INFORMATION: Probe

<400> SEQUENCE: 38

```
gccggtcgtg gccgcg                                                     16
```

<210> SEQ ID NO 39
<211> LENGTH: 19
<212> TYPE: DNA
<213> ORGANISM: Artificial Sequence
<220> FEATURE:
<223> OTHER INFORMATION: Probe

<400> SEQUENCE: 39

```
gactgtcggc gctggggcc                                                  19
```

<210> SEQ ID NO 40
<211> LENGTH: 18
<212> TYPE: DNA
<213> ORGANISM: Artificial Sequence
<220> FEATURE:
<223> OTHER INFORMATION: Probe

<400> SEQUENCE: 40

```
gactgtcggc gctggggc                                                   18
```

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41

```
cggcatgtcg cggatggagc g                                               21
```

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42

```
cggctcgctg tcggtgtacg c                                               21
```

<210> SEQ ID NO 43
<211> LENGTH: 22
<212> TYPE: DNA
<213> ORGANISM: Artificial Sequence
<220> FEATURE:
<223> OTHER INFORMATION: Probe

<400> SEQUENCE: 43

```
ttgacccaca agcgccgact gt                                              22
```

<210> SEQ ID NO 44
<211> LENGTH: 19
<212> TYPE: DNA
<213> ORGANISM: Artificial Sequence
<220> FEATURE:
<223> OTHER INFORMATION: Probe

<400> SEQUENCE: 44
gccccagcgc cgacagtcg                                                19

<210> SEQ ID NO 45
<211> LENGTH: 19
<212> TYPE: DNA
<213> ORGANISM: Artificial Sequence
<220> FEATURE:
<223> OTHER INFORMATION: Probe

<400> SEQUENCE: 45
cgactgtcgg cgttggggc                                                19

<210> SEQ ID NO 46
<211> LENGTH: 21
<212> TYPE: DNA
<213> ORGANISM: Artificial Sequence
<220> FEATURE:
<223> OTHER INFORMATION: Probe

<400> SEQUENCE: 46
cagccagccg agccaattca t                                             21

<210> SEQ ID NO 47
<211> LENGTH: 23
<212> TYPE: DNA
<213> ORGANISM: Artificial Sequence
<220> FEATURE:
<223> OTHER INFORMATION: Probe

<400> SEQUENCE: 47
aattcatgta ccagaacaac ccg                                           23

<210> SEQ ID NO 48
<211> LENGTH: 21
<212> TYPE: DNA
<213> ORGANISM: Artificial Sequence
<220> FEATURE:
<223> OTHER INFORMATION: Probe

<400> SEQUENCE: 48
atggaccaga acccgctgtc g                                             21

<210> SEQ ID NO 49
<211> LENGTH: 21
<212> TYPE: DNA
<213> ORGANISM: Artificial Sequence
<220> FEATURE:
<223> OTHER INFORMATION: Probe

<400> SEQUENCE: 49
aacccgctgt tggggttgac c                                             21

<210> SEQ ID NO 50
<211> LENGTH: 23
<212> TYPE: DNA
<213> ORGANISM: Artificial Sequence
<220> FEATURE:
<223> OTHER INFORMATION: Probe

<400> SEQUENCE: 50
ttgacccgca agcgccgact gtc                                                   23

<210> SEQ ID NO 51
<211> LENGTH: 23
<212> TYPE: DNA
<213> ORGANISM: Artificial Sequence
<220> FEATURE:
<223> OTHER INFORMATION: Probe

<400> SEQUENCE: 51
ttgaccccca agcgccgact gtc                                                   23

<210> SEQ ID NO 52
<211> LENGTH: 23
<212> TYPE: DNA
<213> ORGANISM: Artificial Sequence
<220> FEATURE:
<223> OTHER INFORMATION: Probe

<400> SEQUENCE: 52
ttgacctgca agcgccgact gtc                                                   23

<210> SEQ ID NO 53
<211> LENGTH: 19
<212> TYPE: DNA
<213> ORGANISM: Artificial Sequence
<220> FEATURE:
<223> OTHER INFORMATION: Probe

<400> SEQUENCE: 53
cgactgtggg cgctggggc                                                        19

<210> SEQ ID NO 54
<211> LENGTH: 19
<212> TYPE: DNA
<213> ORGANISM: Artificial Sequence
<220> FEATURE:
<223> OTHER INFORMATION: Probe

<400> SEQUENCE: 54
actgtgggcg ccggggccc                                                        19

<210> SEQ ID NO 55
<211> LENGTH: 18
<212> TYPE: DNA
<213> ORGANISM: Artificial Sequence
<220> FEATURE:
<223> OTHER INFORMATION: Probe

<400> SEQUENCE: 55
agcgccggct ttcggcgc                                                         18

<210> SEQ ID NO 56
<211> LENGTH: 243
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (22)..(22)
<223> OTHER INFORMATION: n can be any nucleotide
<220> FEATURE:
<221> NAME/KEY: misc_feature
<222> LOCATION: (23)..(23)
<223> OTHER INFORMATION: n can be any nucleotide

```
<220> FEATURE:
<221> NAME/KEY: misc_feature
<222> LOCATION: (24)..(24)
<223> OTHER INFORMATION: n can be any nucleotide
<220> FEATURE:
<221> NAME/KEY: misc_feature
<222> LOCATION: (25)..(25)
<223> OTHER INFORMATION: n can be any nucleotide

<400> SEQUENCE: 56
ggatggaacg ggtggtccgg gnnnnggatg accactcagg acgtcgaggc gatcacgccg      60
agacactgat caacatccgc ccggtggtcg ccgccatcaa ggagttcttc ggcaccagcc     120
agctctccca gttcatggac cagaacaacc cgctgtcggg cctcacccac aagcgccggc     180
tttcggcgct ggggccgggc ggtctgtccc gggagcgtgc cgggctggag gtccgcgatg     240
ctc                                                                  243

<210> SEQ ID NO 57
<211> LENGTH: 23
<212> TYPE: DNA
<213> ORGANISM: Artificial Sequence
<220> FEATURE:
<223> OTHER INFORMATION: Probe

<400> SEQUENCE: 57
gacgctgatc aatatccgtc cgg                                             23

<210> SEQ ID NO 58
<211> LENGTH: 22
<212> TYPE: DNA
<213> ORGANISM: Artificial Sequence
<220> FEATURE:
<223> OTHER INFORMATION: Probe

<400> SEQUENCE: 58
cagccagctg tcgcagttca tg                                              22

<210> SEQ ID NO 59
<211> LENGTH: 23
<212> TYPE: DNA
<213> ORGANISM: Artificial Sequence
<220> FEATURE:
<223> OTHER INFORMATION: Probe

<400> SEQUENCE: 59
gttcatggat cagaacaacc ctc                                             23

<210> SEQ ID NO 60
<211> LENGTH: 21
<212> TYPE: DNA
<213> ORGANISM: Artificial Sequence
<220> FEATURE:
<223> OTHER INFORMATION: Probe

<400> SEQUENCE: 60
aaccctctgt cgggcctgac c                                               21

<210> SEQ ID NO 61
<211> LENGTH: 20
<212> TYPE: DNA
<213> ORGANISM: Artificial Sequence
<220> FEATURE:
<223> OTHER INFORMATION: Probe

<400> SEQUENCE: 61
```
acccacaagc gccggctgtc                                              20

<210> SEQ ID NO 62
<211> LENGTH: 17
<212> TYPE: DNA
<213> ORGANISM: Artificial Sequence
<220> FEATURE:
<223> OTHER INFORMATION: Probe

<400> SEQUENCE: 62
ggctgtcggc gctgggc                                                 17

<210> SEQ ID NO 63
<211> LENGTH: 22
<212> TYPE: DNA
<213> ORGANISM: Artificial Sequence
<220> FEATURE:
<223> OTHER INFORMATION: Probe

<400> SEQUENCE: 63
ctgtcgcagt tcatggatca ga                                           22

<210> SEQ ID NO 64
<211> LENGTH: 21
<212> TYPE: DNA
<213> ORGANISM: Artificial Sequence
<220> FEATURE:
<223> OTHER INFORMATION: Primer

<400> SEQUENCE: 64
ccaaaaccag atccgggtcg g                                            21

<210> SEQ ID NO 65
<211> LENGTH: 20
<212> TYPE: DNA
<213> ORGANISM: Artificial Sequence
<220> FEATURE:
<223> OTHER INFORMATION: Primer

<400> SEQUENCE: 65
gtccgggagc ggatgaccac                                              20

<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
gggtgcacgt cgcggacctc                                              20

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
gggcacatcc ggccgtagtg                                              20

<210> SEQ ID NO 68
<211> LENGTH: 18
<212> TYPE: DNA
<213> ORGANISM: Artificial Sequence

```
<220> FEATURE:
<223> OTHER INFORMATION: Probe

<400> SEQUENCE: 68
atccggccgg tcgtcgcc                                                    18

<210> SEQ ID NO 69
<211> LENGTH: 228
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (8)..(8)
<223> OTHER INFORMATION: n can be any nucleotide
<220> FEATURE:
<221> NAME/KEY: misc_feature
<222> LOCATION: (33)..(33)
<223> OTHER INFORMATION: n can be any nucleotide

<400> SEQUENCE: 69
ggcatttnac ggatggaacg cgtggtccgc gancggatga ccacgcagga cgtcgaggcc      60
atcacgccgc agaccctgat caacatccgg ccggtcgtcg ccgcgatcaa ggagttcttc     120
gggaccagcc agctgtcgca gttcatggac cagaacaacc cgctgtcggg tctgacccac     180
aagcgtcgcc tgtcggcgct gggtcccggc ggtctgtccc gtgagcgc                  228

<210> SEQ ID NO 70
<211> LENGTH: 20
<212> TYPE: DNA
<213> ORGANISM: Artificial Sequence
<220> FEATURE:
<223> OTHER INFORMATION: Probe

<400> SEQUENCE: 70
tacggtcggc gagctgatcc                                                  20

<210> SEQ ID NO 71
<211> LENGTH: 19
<212> TYPE: DNA
<213> ORGANISM: Artificial Sequence
<220> FEATURE:
<223> OTHER INFORMATION: Probe

<400> SEQUENCE: 71
tacggcgttt cgatgaacc                                                   19

<210> SEQ ID NO 72
<211> LENGTH: 80
<212> TYPE: DNA
<213> ORGANISM: Artificial Sequence
<220> FEATURE:
<223> OTHER INFORMATION: Probe
<220> FEATURE:
<221> NAME/KEY: CDS
<222> LOCATION: (2)..(79)
<223> OTHER INFORMATION:

<400> SEQUENCE: 72 c agc cag ctg agc caa ttc atg gac cag aac aac ccg ctg tcg ggg ttg     49
  Ser Gln Leu Ser Gln Phe Met Asp Gln Asn Asn Pro Leu Ser Gly Leu
  1               5                  10                  15 acc cac aag cgc cga ctg tcg gcg ctg ggg c                              80
Thr His Lys Arg Arg Leu Ser Ala Leu Gly
            20                  25
```

```
<210> SEQ ID NO 73
<211> LENGTH: 26
<212> TYPE: PRT
<213> ORGANISM: Artificial Sequence
<220> FEATURE:
<223> OTHER INFORMATION: Probe

<400> SEQUENCE: 73

Ser Gln Leu Ser Gln Phe Met Asp Gln Asn Asn Pro Leu Ser Gly Leu
1               5                   10                  15

Thr His Lys Arg Arg Leu Ser Ala Leu Gly
            20                  25
```

METHOD FOR THE DETECTION OF THE ANTIBIOTIC RESISTANCE SPECTRUM OF MYCOBACTERIUM SPECIES

CROSS-REFERENCE TO RELATED APPLICATIONS

The present application is a divisional of allowed application Ser. No. 09/722,319, filed Nov. 28, 2000, now U.S. Pat. No. 6,632,607 which is a continuation of application Ser. No. 08/750,088, now U.S. Pat. No. 6,329,138 B1, issued Dec. 11, 2001; which is a national phase application of International application Ser. No. PCT/EP95/02230, International Application date Jun. 9, 1995, 35 U.S.C. § 371 date Feb. 21, 1997, which International Application designates the United States of America and was published in English as International Publication No. WO 95/3385 1, publication date Dec. 14, 1995; the present application claims priority under 35 U.S.C § 119 to European Application EP 94870093.5, filed Jun. 9, 1994.

The present invention relates to the field of drug-resistant mycobacteria.

The present invention relates to probes, primers, methods and kits comprising the same for the detection of mycobacterial nucleic acids in biological samples.

Identification of most clinically relevant *Mycobacterium* species, in particular of *Mycobacterium tuberculosis* is tedious and time consuming due to culture-procedures which can take up to 6 weeks. Rapid diagnosis of *Mycobacterium* infection is very important since the disease might be life-threatening and highly contagious. Only recently some methods—all making use of one or another amplification process—have been developed to detect and identify *Mycobacterium* species without the need for culture (Claridge et al. 1993). Most of these methods are still in evaluation and their benefit in routine applications remains questionable. Moreover, these methods do not solve the problem of *Mycobacterium* drug-resistance detection which still relies on culture.

Since the frequency of multidrug resistance in tuberculosis is steadily increasing (Culliton, 1992), it is clear now that early diagnosis of *M. tuberculosis* and the rapid recognition of resistance to the major tuberculostatics are essential for therapy and an optimal control of the resurgent epidemic.

The antibiotics used for treatment of *M. tuberculosis* infections are mainly isoniazid and rifampicini either administered separately or as a combination of both. Occasionally, pyrazinamide, ethambutol and streptomycin are used: other classes of antibiotics like (fluoro)quinolones may become the preferred tuberculostatics in the future.

Since most multidrug resistant mycobacteria also lost susceptibility to rifampicin, rifampicin-resistance is considered to be a potential marker for multidrug resistant tuberculosis. For this reason, the detection of resistance to rifampicini might be of particular relevance.

For the majority of the *M. tuberculosis* strains examined so far, the mechanism responsible for resistance to rifampicin (and analogues like rifabutin) has been elucidated. Rifampicin (and analogues) block the RNA polymerase by interacting with the β-subunit of this enzyme. Telenti et al. (1993a) found that mutations in a limited region of the β-subunit of the RNA polymerase of *M. tuberculosis* give rise to insensitivity of the RNA polymerase for rifampicin action. This region is limited to a stretch of 23 codons in the rpoB gene. The authors describe 17 amino acid changes provoking resistance to rifampicin (Telenti et al. 1993b). These amino acid changes are caused by point mutations or deletions at 15 nucleotides or 8 amino acid codons respectively scattered over a stretch of 67 nucleotides or 23 amino acid codons.

Telenti et al. (1993a and b) described a PCR-SSCP method to screen for the relevant mutations responsible for rifampicin resistance (SSCP refers to single-strand conformation polymorphism). SSCP analysis can be performed either by using radio-activity or by using fluorescent markers. In the latter case sophisticated and expensive equipment (an automated DNA-sequencing apparatus) is needed. The SSCP approach described has also other limitations with respect to specificity and sensitivity which might impede its routine use. Specimen can only be adequately analysed directly if a significant load of bacteria (microscopy score: >90 organisms/field) is observed microscopically and on crude DNA samples strand-separation artefacts may be observed which complicate the interpretation of the results.

Kapur et al. (1994) describe 23 distinct rpoB alleles associated with rifampicin resistance. In addition to the mutations described by Telenti et al. (1993a), some new mutant rpoB alleles are described. However, the most frequently occuring alleles remain the same as those described before.

In *M. leprae*, the molecular basis for rifampicin resistance was described by Honoré and Cole (1993). Here too, resistance stemmed from mutations in the rpoB gene, which encodes the beta subunit of RNA polymerase of *M. leprae*. Only a limited number of resistant *M. leprae* strains (9) were analysed, and in most of them (8/9) resistance was due to a mutation affecting the Ser-425 residue.

Clinically important mycobacteria other than *M. tuberculosis* and *M. leprae* often show an innate, be it variable, resistance to rifampicin. This is the case for *M. avium* and *M. intracellulare*, human pathogens for which only limited treatment options are available. Guerrero et al. (1994) compared the rpoB-gene sequences of different *M. avium* and *M. intracellulare* isolates with that of *M. tuberculosis*. Differences are present at the nucleotide level but a full amino acid identity was found with rifampicin-sensitive *M. tuberculosis*. These findings suggest that another mechanism of resistance, possibly a permeability barrier, applies for *M. avium* and *M. intracellulare*.

The specific detection of point mutations or small deletions can elegantly be approached using hybridization procedures such as the reverse hybridization assay. However, the complexity observed in the relevant part of the rpoB gene does not allow a straightforward probe development. As will be exemplified further, it was one of the objects of the present invention to design a specific approach allowing the detection of most if not all mutations found so far in a fast and convenient way without the need for sophisticated equipment.

The mechanism of resistance to isoniazid (INH) is considerably more complex than that for rifampicin. At least two gene products are involved in INH-resistance. First, there is catalase-peroxidase which is believed to convert INH to an activated molecule. Hence, strains which do not produce catalase-peroxidase by virtue of a detective or deleted katG gene are not anymore susceptible to INH (Zhang et al. 1992: Stoeckle et al. 1993). In this context it should be mentioned that the association between INH-resistance and the loss of catalase activity was already noted in the fifties (Middlebrook, 1954 a and b; Youatt, 1969).

The second molecule involved is the inhA gene product, which is believed to play a role in the mycolic acid biosynthesis. It is postulated that the activated INH molecule interacts either directly or indirectly with this product and probably prevents proper mycolic acid biosynthesis. This hypothesis is based on the recent observation that overexpression of the wild type inhA gene or a particular amino acid change (S94A) in the inhA gene product confers resistance to INH (Banerjee et al., 1994).

In short, and somewhat simplified we can state that in certain *M. tuberculosis* strains resistance to INH might be mediated by:
- the loss of catalase-peroxidase activity the presence of certain amino acid changes in the inhA protein the expression level of the wild type inhA protein Also, other mechanisms might be involved in confering resistance to INH and related drugs. The importance of these factors in the total spectrum of INH-resistance mechanisms has yet to be assessed. This issue can be addressed by means of DNA probe techniques if reliable DNA probes can be developed from the available DNA-sequences of the katG gene (EMBL n° X68081) and inhA gene (EMBL n° U02492) of *M. tuberculosis*. These probe-tests could then also be applied for detection of drug resistance in biological samples.

For the detection of resistance to streptomycine and (fluoro)quinolones the same approach as for rifampicin can be followed. Resistance to these antibiotics is also induced by point mutations in a limited region of one or more genes. Point mutations in the gyrase gene confer resistance to (fluoro)quinolones (EMBL n° L27512). Streptomycin resistance is correlated with mutations in either the 16S rRNA gene or the gene of a ribosomal protein S12 (rpsL) (Finken et al., 1993: Douglas and Steyn, 1993: Nair et al. 1993).

Resistance due to nucleotide changes in the katG, rpoB and rpsL genes have been described in international application WO 93/22454. For each of the different genes in *M. tuberculosis* only one of the many possible mutations was specified in detail, n1. R461L for katG. S425L (equivalent to S531L described by Telenti et al. and the present invention) for rpoB and K42R for rpsL.

It is an object of the present invention to provide a rapid and reliable detection approach for determination of antibiotic resistance of mycobacterial species present in a biological sample.

More particularly, it is an aim of the present invention to provide a rapid and reliable method for determination of resistance to rifampicin (and/or rifabutin) of *M. tuberculosis* present in a biological sample.

It is also an object of the present invention to provide methods enabling the detection and identification of *Mycobacterium* species in a biological sample, directly coupled to the monitoring of the antibiotic resistance spectrum.

It is more particularely an aim of the present invention to provide a method to detect the presence of *Mycobacterium tuberculosis* in a biological sample directly coupled to the detection of rifampicin, (and/or rifabutin) resistance.

It is more particularely an aim of the present invention to provide a method to detect the presence of *Mycobacterium leprae* in a biological sample directly coupled to the detection of rifampicin (and/or rifabutin) resistance.

It is also an aim of the present invention to select particular probes able to discriminate wild-type sequences from mutated sequences conferring resistance to one or more drugs.

It is more particularly an aim of the present invention to select particular probes able to discriminate wild-type sequences from mutated sequences conferring resistance to rifampicin (and/or rifabutin).

It is more particularly an aim of the present invention to select a particular set of probes, able to discriminate wild-type sequences from mutated sequences conferring resistance to rifampicin (an/or rifabutin) with this particular set of probes being used under the same hybridisation and wash-conditions.

It is moreover an aim of the present invention to combine a set of selected probes able to discriminate wild-type sequences from mutated sequences conferring resistance to rifampicin (and/or rifabutin) with another set of selected probes able to identify the mycobacteria species present in the biological sample, whereby all probes can be used under the same hybridisation and wash-conditions.

It is also an aim of the present invention to select primers enabling the amplification of the gene fragment(s) determining the antibiotic resistance trait of interest.

It is more particularly an aim of the present invention to select primers enabling the amplification of the rpoB-gene fragment determining resistance to rifampicin (and analogues).

Another aim of the invention is to provide kits for the detection of antibiotic resistance in mycobacteria, possibly coupled to the identification of the mycobacterial species involved.

All the aims of the present invention have been met by the following specific embodiments.

The selection of the preferred probes of the present invention is based on the Line Probe Assay (LiPA) principle which is a reverse hybridization assay using oligonlucleotide probes immobilized as parallel lines on a solid support strip (Stuyver et al. 1993; international application WO 94/12670). This approach is particularly advantageous since it is fast and simple to perform. The reverse hybridization format and more particularly the LiPA approach has many practical advantages as compared to other DNA techniques or hybridization formats, especially when the use of a combination of probes is preferable or unavoidable to obtain the relevant information sought.

It is to be understood, however, that any other type of hybridization assay or format using any of the selected probes as described further in the invention, is also covered by the present invention.

The reverse hybridization approach implies that the probes are immobilized to a solid support and that the target DNA is labelled in order to enable the detection of the hybrids formed.

The following definitions serve to illustrate the terms and expressions used in the present invention.

The target material in these samples may either be DNA or RNA e.g. genomic DNA or messenger RNA or amplified versions thereof. These molecules are also termed polynucleic acids.

The term "probe" refers to single stranded sequence-specific oligonucleotides which have a sequence which is complementary to the target sequence to be detected.

The term complementary as used herein means that the sequence of the single stranded probe is exactly complementary to the sequence of the single-stranded target, with the target being defined as the sequence where the mutation to be detected is located. Since the current application requires the detection of single basepair mismatches, very stringent conditions for hybridization are required, allowing in principle only hybridization of exactly complementary sequences. However, variations are possible in the length of the probes (see below), and it should be noted that, since the central part of the probe is essential for its hybridization characteristics, possible deviations of the probe sequence versus the target sequence may be allowable towards head and tail of the probe, when longer probe sequences are used. These variations, which may be conceived from the common knowledge in the art, should however always be evaluated experimentally, in order to check if they result in equivalent hybridization characteristics than the exactly complementary probes.

Preferably, the probes are about 5 to 50 nucleotides long, more preferably from about 10 to 25 nucleotides. The nucleotides as used in the present invention may be ribonucleotides, deoxyribonucleotides and modified nucleotides such as inosine or nucleotides containing modified groups which do not essentially alter their hybridisation characteristics. Probe sequences are represented throughout the specification as single stranded DNA oligonucleotides from the 5' to the 3' end. It is obvious to the man skilled in the art that any of the below-specified probes can be used as such, or in their complementary form, or in their RNA form (wherein T is replaced by U).

The probes according to the invention can be prepared by cloning of recombinant plasmids containing inserts including the corresponding nucleotide sequences, if need be by cleaving the latter out from the cloned plasmids upon using the adequate nucleases and recovering them, e.g. by fractionation according to molecular weight. The probes according to the present invention can also be synthesized chemically, for instance by the conventional phospho-triester method.

The term "solid support" can refer to any substrate to which an oligonucleotide probe can be coupled, provided that it retains its hybridization characteristics and provided that the background level of hybridization remains low. Usually the solid substrate will be a microtiter plate, a membrane (e.g. nylon or nitrocellulose) or a microsphere (bead). Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, $NH_2$ groups, SH groups, carboxylic groups, or coupling with biotin, haptens or proteins.

The term "labelled" refers to the use of labelled nucleic acids. Labelling may be carried out by the use of labelled nucleotides incorporated during the polymerase step of the amplification such as illustrated by Saiki et al. (1988) or Bei et al. (1990) or labelled primers, or by any other method known to the person skilled in the art. The nature of the label may be isotopic ($^{32}P$, $^{35}S$, etc.) or non-isotopic (biotin, digoxigenin, etc.).

The term "primer" refers to a single stranded oligonucleotide sequence capable of acting as a point of initiation for synthesis of a primer extension product which is complementary to the nucleic acid strand to be copied. The length and the sequence of the primer must be such that they allow to prime the synthesis of the extension products. Preferably the primer is about 5-50 nucleotides long. Specific length and sequence will depend on the complexity of the required DNA or RNA targets, as well as on the conditions of primer use such as temperature and ionic strenght.

The fact that amplification primers do not have to match exactly with the corresponding template sequence to warrant proper amplification is amply documented in the literature (Kwok et al., 1990).

The amplification method used can be either polymerase chain reaction (PCR; Saiki et al. 1988), ligase chain reaction (LCR: Landgren et al., 1988; Wu & Wallace, 1989; Barany, 1991), nucleic acid sequence-based amplification (NASBA; Guatelli et al., 1990; Compton, 1991), transcription-based amplification system (TAS; Kwoh et al., 1989), strand displacement amplification (SDA; Duck. 1990; Walker et al. 1992) or amplification by means of Qβ replicase (Lizardi et al. 1988; Lomeli et al., 1989) or any other suitable method to amplify nucleic acid molecules known in the art.

The oligonucleotides used as primers or probes may also comprise nucleotide analogues such as phosphorothiates (Matsukura et al., 1987), alkylphosphorothiates (Miller et al. 1979) or peptide nucleic acids (Nielsen et al. 1991; Nielsen et al., 1993), or may contain intercalating agents (Asseline et al. 1984).

As most other variations or modifications introduced into the original DNA sequences of the invention these variations will necessitate adaptions with respect to the conditions under which the oligonucleotide should be used to obtain the required specificity and sensitivity. However the eventual results of hybridisation will be essentially the same as those obtained with the unmodified oligonucleotides.

The introduction of these modifications may be advantageous in order to positively influence characteristics such as hybridization kinetics, reversibility of the hybrid-formation, biological stability of the oligonucleotide molecules, etc.

The "sample" may be any biological material taken either directly from the infected human being (or animal), or after culturing (enrichment). Biological material may be e.g. expectorations of any kind, broncheolavages, blood, skin tissue, biopsies, lymphocyte blood culture material, colonies, liquid cultures, soil, faecal samples, urine etc.

The probes of the invention are designed for attaining optimal performance under the same hybridization conditions so that they can be used in sets for simultaneous hybridization; this highly increases the usefulness of these probes and results in a significant gain in time and labour. Evidently, when other hybridization conditions would be preferred, all probes should be adapted accordingly by adding or deleting a number oft nucleotides at their extremities. It should be understood that these concomitant adaptations should give rise to essentially the same result, namely that the respective probes still hybridize specifically with the defined target. Such adaptations might also be necessary if the amplified material should be RNA in nature and not DNA as in the case for the NASBA system.

For designing probes with desired characteristics, the following useful guidelines known to the person skilled in the art can be applied.

Because the extent and specificity of hybridization reactions such as those described herein are affected by a number of factors, manipulation of one or more of those factors will determine the exact sensitivity and specificity of a particular probe, whether perfectly complementary to its target or not. The importance and effect of various assay conditions, explained further herein, are known to those skilled in the art.

First, the stability of the [probe:target] nucleic acid hybrid should be chosen to be compatible with the assay conditions. This may be accomplished by avoiding long AT-rich sequences, by terminating the hybrids with G:C base pairs, and by designing the probe with an appropriate Tm. The beginning and end points of the probe should be chosen so that the length and % GC result in a Tm about 2-10° C. higher than the temperature at which the final assay will be performed. The base composition of the probe is significant because G-C base pairs exhibit greater thermal stability as compared to A-T base pairs due to additional hydrogen bonding. Thus, hybridization involving complementary nucleic acids of higher G-C content will be stable at higher temperatures.

Conditions such as ionic strenght and incubation temperature under which a probe will be used should also be taken into account when designing a probe. It is known that hybridization will increase as the ionic strenght of the reaction mixture increases, and that the thermal stability of the hybrids will increase with increasing ionic strenght. On the other hand, chemical reagents, such as formamide, urea, DMSO and alcohols, which disrupt hydrogen bonds, will increase the stringency of hybridization. Destabilization of the hydrogen bonds by such reagents can greatly reduce the Tm. In general, optimal hybridization for synthetic oligonucleotide probes of about 10-50 bases in length occurs approximately 5° C. below the melting temperature for a given duplex. Incubation at temperatures below the optimum may allow mismatched base sequences to hybridize and can therefore result in reduced specificity.

It is desirable to have probes which hybridize only under conditions of high stringency. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. The degree of stringency is chosen such as to maximize the difference in stability between the hybrid formed with the target and the nontarget nucleic acid. In the present case, single base pair changes need to be detected, which requires conditions of very high stringency.

Second, probes should be positioned so as to minimize the stability of the [probe:nontarget] nucleic acid hybrid. This may be accomplished by minimizing the length of perfect complementarity to non-target organisms, by avoiding GC-rich regions of homology to non-target sequences, and by positioning the probe to span as many destabilizing mismatches as possible. Whether a probe sequence is useful to detect only a specific type of organism depends largely on the thermal stability difference between [probe:target] hybrids and [probe:non-target] hybrids. In designing probes, the differences in these Tm values should be as large as possible (e.g. at least 2° C. and preferably 5° C.).

The length of the target nucleic acid sequence and, accordingly, the length of the probe sequence can also be important. In some cases, there may be several sequences from a particular region, varying in location and length, which will yield probes with the desired hybridization characteristics. In other cases, one sequence may be significantly better than another which differs merely by a single base. While it is possible for nucleic acids that are not perfectly complementary to hybridize, the longest stretch of perfectly complementary base sequence will normally primarily determine hybrid stability. While oligonucleotide probes of different lengths and base composition may be used, preferred oligonucleotide probes of this invention are between about 5 to 50 (more particularely 10-25) bases in length and have a sufficient stretch in the sequence which is perfectly complementary to the target nucleic acid sequence.

Third, regions in the target DNA or RNA which are known to form strong internal structures inhibitory to hybridization are less preferred. Likewise, probes with extensive self-complementarity should be avoided. As explained above, hybridization is the association of two single strands of complementary nucleic acids to form a hydrogen bonded double strand. It is implicit that if one of the two strands is wholly or partially involved in a hybrid that it will be less able to participate in formation of a new hybrid. There can be intramolecular and intermolecular hybrids formed within the molecules of one type of probe if there is sufficient self complementarity. Such structures can be avoided through careful probe design. By designing a probe so that a substantial portion of the sequence of interest is single stranded, the rate and extent of hybridization may be greatly increased. Computer programs are available to search for this type of interaction. However, in certain instances, it may not be possible to avoid this type of interaction.

The present invention provides in its most general form for a method to detect the antibiotic resistance spectrum of *Mycobacterium* species present in a sample, possibly coupled to the identification of the *Mycobacterium* species involved, comprising the steps of:
(i) if need be releasing, isolating or concentrating the polynucleic acids present in the sample;
(ii) if need be amplifying the relevant part of the antibiotic resistance genes present in said sample with at least one suitable primer pair;
(iii) hybridizing the polynucleic acids of step (i) or (ii) with at least one of the rpoB gene probes as mentioned in table 2, under appropiate hybridization and wash conditions;
(iv) detecting the hybrids formed in step (iii);
(v) inferring the *Mycobacterium* antibiotic resistance spectrum, and possibly the *Mycobacterium* species involved from the differential hybridization signal(s) obtained in step (iv).

The relevant part of the antibiotic resistance genes refers to the regions in the p B, katG, inhA, 16S rRNA, rpsL and gyrase genes harboring mutations causing resistance to rifampicin, isoniazid, streptomycin and (fluoro)quinolones as described above.

According to a preferred embodiment of the present invention, step (iii) is performed using a set of probes meticulously designed as such that they show the desired hybridization results, when used under the same hybridization and wash conditions.

More specifically, the present invention provides a method for detection of rifampicin (and/or rifabutin) resistance of *M. tuberculosis* present in a biological sample, comprising the steps of:
(i) if need be releasing, isolating or concentrating the polynucleic acids present in the sample;
(ii) if need be amplifying the relevant part of the rpoB gene present in said polynucleic acids with at least one suitable primer pair:
(iii) hybridizing the polynucleic acids of step (i) or (ii) with a selected set of rpoB wild-type probes under appropiate hybridization and wash conditions, with said set comprising at least one of the following probes (see Table 2):

| | |
|---|---|
| S1 | (SEQ ID NO 1) |
| S11 | (SEQ ID NO 2) |
| S2 | (SEQ ID NO 3) |
| 53 | (SEQ ID NO 4) |
| S33 | (SEQ ID NO 5) |
| S4 | (SEQ ID NO 6) |
| S44 | (SEQ ID NO 7) |
| S444 | (SEQ ID NO 43) |
| S4444 | (SEQ ID NO 8) |
| S5 | (SEQ ID NO 9) |
| S55 | (SEQ ID NO 10) |
| S555 | (SEQ ID NO 39) |
| S5555 | (SEQ ID NO 40) |
| S55C | (SEQ ID NO 44) |

-continued

| | |
|---|---|
| S55M | (SEQ ID NO 45) |
| S6 | (SEQ ID NO 11) |
| S66 | (SEQ ID NO 12) |

(iv) detecting the hybrids formed in step (iii);
(v) inferring the rifampicin susceptibility (sensitivity versus resistance) of *M. tuberculosis* present in the sample from the differential hybridization signal(s) obtained in step (iv).

The term susceptibility refers to the phenotypic characteristic of the *M. tuberculosis* strain being either resistant or sensitive to the drug, as determined by in vitro culture methods, more specifically to rifampicin (and/or rifabutin). Resistance to rifampicin is revealed by the absence of hybridization with at least one of the S-probes.

Standard hybridization and wash conditions are for instance 3×SSC (Sodium Saline Citrate). 20% deionized FA (Formamide) at 50° C. Other solutions (SSPE (Sodium saline phosphate EDTA), TMACl (Tetramethyl ammonium Chloride), etc.) and temperatures can also be used provided that the specificity and sensitivity of the probes is maintained. If need be, slight modifications of the probes in length or in sequence have to be carried out to maintain the specificity and sensitivity required under the given circumstances. Using the probes of the invention, changing the conditions to 1.4×SSC. 0.07% SDS at 62° C. lead to the same hybridisation results as those obtained under standard conditions, without the necessity to adapt the sequence or length of the probes.

Suitable primer pairs can be chosen from a list of primer pairs as described below.

In a more preferential embodiment, the above-mentioned polynucleic acids from step (i) or (ii) are hybridized with at least two, three, four, five, six, seven, eight, nine, ten, eleven, twelve, thirteen, fourteen, fifteen, sixteen or seventeen of the above-mentioned S-probes, preferably with 5 or 6 S-probes, which, taken together, cover the "mutation region" of the rpoB gene.

The term "mutation region" means the region in the rpoB-gene sequence where most, if not all of the mutations responsible for rifampicin resistance are located. This mutation region is represented in FIG. 1.

In a more preferential embodiment, the above-mentioned polynucleic acids from step (i) or (ii) are hybridized with a selected set of rpoB-wild-type probes, with said set comprising at least one, and preferentially all of the following probes (see Table 2):

| | |
|---|---|
| S11 | (SEQ ID NO 2) |
| S2 | (SEQ ID NO 3) |
| S33 | (SEQ ID NO 5) |
| S4444 | (SEQ ID NO 8) |
| S55 or S5555 | (SEQ ID NO 10 or 40) |

In another particular embodiment the set of S-probes as described above, or at least one of them, can be combined with one or more SIL-probes, detecting silent mutations in the rpoB gene. A preferential SIL-probe is SIL-1 (SEQ ID NO 13, see Table 2).

In another embodiment of the invention, the set of S-probes and possibly SIL-probes, can be combined with at least one R-probe detecting a specific mutation associated with rifampicin-resistance.

R-probes are selected from the following group of probes (see Table 2):

| | |
|---|---|
| R1 | (SEQ ID NO 46) |
| R2 | (SEQ ID NO 14) |
| R2B | (SEQ ID NO 47) |
| R2C | (SEQ ID NO 48) |
| R3 | (SEQ ID NO 49) |
| R4A | (SEQ ID NO 15) |
| R44A | (SEQ ID NO 16) |
| R444A | (SEQ ID NO 17) |
| R4B | (SEQ ID NO 18) |
| R44B | (SEQ ID NO 19) |
| R444B | (SEQ ID NO 20) |
| R4C | (SEQ ID NO 50) |
| R4D | (SEQ ID NO 51) |
| R4E | (SEQ ID NO 52) |
| R5 | (SEQ ID NO 21) |
| R55 | (SEQ ID NO 22) |
| R5B | (SEQ ID NO 53) |
| R5C | (SEQ ID NO 54) |

Preferably the set of S-probes and possibly SIL-probes can be combined with at least two, three, four, five, six, or more R probes.

Most preferably, the set of S-probes and possibly SIL-probes are combined with at least one R-probe from the following restricted group of probes

| | |
|---|---|
| R2 | (SEQ ID NO 14) |
| R444A | (SEQ ID NO 17) |
| R444B | (SEQ ID NO 20) |
| R55 | (SEQ ID NO 22) |

In the case where S and R probes are combined, resistance to rifampicin is revealed by absence of hybridization with one of the S-probes and possibly by a positive hybridization signal with the corresponding R-probe.

Since some mutations may be more frequently occurring than others, e.g. in certain geographic areas (see e.g. Table 5) or in specific circumstances (e.g. rather closed communities) it may be appropiate to screen only for specific mutations, using a selected set of S and/or R probes. This would result in a more simple test, which would cover the needs under certain circumstances. According to Telenti et al. (1993a and b) most mutations described in his publication are relatively rare (3% or less): predominant mutations are S531L (51.6%). H526Y (12.5%), D516V (9.4%) and H1526D (7.8%).

In a particular embodiment of the invention a selected set of two or three S-probes is used, the respective sets of probes being:

| | |
|---|---|
| S4444 | (SEQ ID NO 8) |
| S55 (or S5555) | (SEQ ID NO 10 or 40) |
| S2 | (SEQ ID NO 3) |
| S4444 | (SEQ ID NO 8) |
| S55 (or S5555) | (SEQ ID NO 10 or 40) |

Using this restricted sets of S-probes the majority of rifampicin resistant cases can be detected, by an absence oft hybridisation signal with at least one of these probes.

In another particular embodiment of the invention, at least one R probe is used, possibly combined with a selected set of two or three S probes as described above, said R probe being chosen from the following list of probes:

| | |
|---|---|
| R2 | (SEQ ID NO 14) |
| R444A | (SEQ ID NO 17) |
| R444B | (SEQ ID NO 20) |
| R55 | (SEQ ID NO 22) |

In this case, the specific mutation responsible for the rifampicin-resistant phenotype can be inferred from a positive hybridization signal with one of the R-probes and/or the absence of hybridization with the corresponding S-probe.

In another embodiment of the invention, the above-mentioned S, SIL or R probes may be combined with at least one species-specific probe for *M. tuberculosis* allowing simultaneous identification of *Mycobacterium tuberculosis* and detection of rifampicin resistance, with said species-specific probe being chosen from the following group of probes (see Table 2):

| | |
|---|---|
| MT-POL-1 | (SEQ ID NO 23) |
| MT-POL-2 | (SEQ ID NO 24) |
| MT-POL-3 | (SEQ ID NO 25) |
| MT-POL-4 | (SEQ ID NO 26) |
| MT-POL-5 | (SEQ ID NO 27) |
| Most preferably the species-specific | |
| *M. tuberculosis* proce is: | |
| MT-POL-1 | (SEQ ID NO 23) |

In yet another embodiment of the invention, the above-mentioned S, SIL, R or, MT-POL probes can be combined with at least one species-specific probe for *M. paratuberculosis*, *M. avium*, *M. scrophulaceum*, *M. kansasii*, *M. intracellulare* (and MAC-strains) or *M. leprae*, with said probes being respectively MP-POL-1 (SEQ ID NO 28), MA-POL-1 (SEQ ID NO 29), MS-POL-1 (SEQ ID NO 38), MK-POL-1 (SEQ ID NO 55), MI-POL-1 (SEQ ID NO 68) and ML-POL-1 (SEQ ID NO 57) (see table 2B) or any species-specific probe derived from the sequence of the relevant part of the rpoB gene of *M. paratuberculosis* (SEQ ID NO 35), *M. avium* (SEQ ID NO 36), *M. scrofulaceum* (SEQ ID NO 37), *M. kansasii* (SEQ ID NO 56) or MAC-strains (SEQ ID NO 69), as represented respectively in FIGS. 5, 6, 7, 8 and 11. It should be noted that the sequences represented in FIGS. 5-8 and 11 are new. The sequence of the rpoB-gene fragment of *M. intracellulare* and *M. leprae* has been described by others (Guerrero et al. 1994; Honoré and Cole, 1993).

The term "MAC-strains" means "*M. avium* complex" strains known to the man skilled in the art of mycobacteria taxonomy. This rather heterogeneous group of MAC-strains may however comprise strains which are genotypically rather like *M. intracellulare*. This is also the case for isolate ITG 926, of which the rpoB sequence is shown in FIG. 11. The MI-POL-1 probe derived from SEQ ID NO 69 and the published *M. intracellulare* rpoB sequence is therefor specific for *M. intracellulare* and some MAC strains together.

It should be stressed that all of the above-mentioned probes, including the species-specific probes, are contained in the sequence of the rpoB gene, and more particulary in the sequence of the amplified rpoB gene fragment. Moreover, as illustrated further in the examples, the probes described above as "preferential", are designed in such a way that they can all be used simultaneously, under the same hybridization and wash conditions. These two criteria imply that a single amplification and hybridization step is sufficient for the simultaneous detection of rifampicin resistance and the identification of the mycobacterial species involved.

In a preferential embodiment, and by wart of an example, a method is disclosed to detect *M. tuberculosis* and its resistance to rifampicin, comprising the steps of:

(i) if need be releasing, isolating or concentrating the polynucleic acids present in the sample;

(ii) if need be amplifying the relevant part of the rpoB gene with at least one suitable primer pair;

(iii) hybridizing the polynucleic acids of step (i) or (ii) with the following set of probes under appropriate hybridization and wash conditions MT-POL-1
S11
S33
S4444
S55 or S5555
R2
R444A
R444B
R55

(iv) detecting the hybrids formed in step (iii);

(v) inferring the presence of *M. tuberculosis* and its susceptibility to rifampicin from the differential hybridization signal(s) obtained in step (iv).

In order to detect the mycobacterial organisms and/or their resistance pattern with the selected set of oligonucleotide probes, any hybridization method known in the art can be used (conventional dot-blot, Southern blot, sandwich, etc.).

However, in order to obtain fast and easy results if a multitude of probes are involved, a reverse hybridization format may be most convenient.

In a preferred embodiment the selected set of probes are immobilized to a solid support. In another preferred embodiment the selected set of probes are immobilized to a membrane strip in a line fashion. Said probes may be immobilized individually or as mixtures to delineated locations on the solid support.

A specific and very user-friendly embodiment of the above-mentioned preferential method is the LiPA method, where the above-mentioned set of probes is immobilized in parallel lines on a membrane, as further described in the examples.

The above mentioned R-probes detect mutations which have already been described in the prior art (Telenti et al., 1993a and 1993b). However, as illustrated further in the examples, four new mutations associated with rifampicin-resistance in *M. tuberculosis*, not yet described by others, are disclosed by the current invention. Using the S-probes of the current invention, new mutations as well as mutations already described in the prior art can be detected. The unique concept of using a set of S-probes covering the complete mutation region in the rpoB gene, allows to detect most, if not all of the mutations in the rpoB-gene responsible for rifampicin resistance, even those mutations which would not yet have been described uptil now.

The four new rpoB mutations (D516G, H526C, H526T and R529Q) are marked in Table 1 with an asterisk. By way of an example, the sequence of the SB-mutant allele H526C is represented in FIG. 2 (SEQ ID NO 34).

The invention also provides for any probes or primersets designed to specifically detect or amplify specifically these new rpoB gene mutations, and any method or kits using said primersets or probes.

In another embodiment, the invention also provides for a method for detection of rifampicin (and/or rifabutin) resistance of *M. leprae* present in a biological sample, comprising the steps of:

(i) if need be releasing, isolating or concentrating the polynucleic acids present in the sample;

(ii) if need be amplifying the relevant part of the rpoB gene with at least one suitable primer pair;

(iii) hybridizing the polynucleic acids of step (i) or (ii) with a selected set of rpoB wild-type probes under appropiate hybridization and wash conditions, with said set comprising at least one of the following probes (see Table 2):

| | |
|---|---|
| ML-S1 | (SEQ ID NO 58) |
| ML-S2 | (SEQ ID NO 59) |
| ML-S3 | (SEQ ID NO 60) |
| ML-S4 | (SEQ ID NO 61) |
| ML-S5 | (SEQ ID NO 62) |
| ML-S6 | (SEQ ID NO 63) |

(iv) detecting the hybrids formed in step (iii);

(v) inferring the rifampicin susceptibility (sensitivity versus resistance) of *M. leprae* present in the sample from the differential hybridization signal(s) obtained in step (iv).

Resistance to rifampicin is revealed by the absence of hybridization with at least one of the ML-S-probes.

In another embodiment of the invention, the above-mentioned ML-S probes may be combined with a species specific probe for *M. leprae*. ML-POL-1, allowing simultaneous identification of *M. leprae* and detection of rifampicin resistance, with said species specific probe being represented in SEQ ID NO 57.

It is to be noted that the above-mentioned ML-S probes and ML-POL-1 probe are all contained within the same amplified rpoB-gene fragment of *M. leprae*, and are designed as such that they can all be used under the same hybridization and wash conditions.

The invention further provides for any of the probes as described above, as wemm as compositions comprising at least one of these probes.

The invention also provides for a set of primers, allowing amplification of the mutation region of the rpoB gene of *M. tuberculosis*. The sets of primers can be chosen from the following group of sets (see table 2):

| | |
|---|---|
| P1 and P5 | (SEQ ID NO 30 and 33) |
| P3 and P4 | (SEQ ID NO 31 and 32) |
| P7 and P8 | (SEQ ID NO 41 and 42) |
| P2 and P6, in combination with (P1 and P5) or (P3 and P4) or (P7 and P8) Most preferably, the set of primers is the following: | |
| P3 and P4 | (SEQ ID NO 31 and 32). |

The invention also provides for a set of primers allowing amplification of the mutation region of the rpoB gene in mycobacteria in general, i.e. in at least *M. tuberculosis, M. avium, M. paratuberculosis, M. intracellulare, M. leprae, M. scrofulaceuin*. These general primers can be used e.g. in samples where the presence oft mycobacteria other than *M. tuberculosis* is suspected, and where it is desirable to have a more general detection method.

The set of primers is composed of a 5'-primer, selected from the following set:

| | |
|---|---|
| MGRPO-1 | (SEQ ID NO 64) |
| MGRPO-2 | (SEQ ID NO 65) | and a 3'-primer, selected from the following set:

| | |
|---|---|
| MGRPO-3 | (SEQ ID NO 66) |
| MGRPO-4. | (SEQ ID NO 67) |

The sequence of these primers is shown in Table 2B.

Primers may be labeled with a label of choice (e.g. biotine). Different primer-based target amplification systems may be used, and preferably PCR-amplification, as set out in the examples. Single-round or nested PCR may be used.

The invention also provides for a kit for inferring the antibiotic resistance spectrum of mycobacteria present in a biological sample, possibly coupled to the identification of the mycobacterial species involved, comprising the following components:

(i) when appropiate, a means for releasing, isolating or concentrating the polynucleic acids present in the sample;

(ii) when appropriate, at least one of the above-defined set of primers;

(iii) at least one of the probes as defined above, possibly fixed to a solid support;

(iv) a hybridization buffer, or components necessary for producing said buffer;

(v) a wash solution, or components necessary for producing said solution;

(vi) when appropriate, a means for detecting the hybrids resulting from the preceding hybridization.

The term "hybridization buffer" means a buffer enabling a hybridization reaction to occur between the probes and the polynucleic acids present in the sample, or the amplified products, under the appropiate stringency conditions.

The term "wash solution" means a solution enabling washing of the hybrids formed under the appropiate stringency conditions.

More specifically, the invention provides for a kit as described above, for the simultaneous detection of *M. tuberculosis* and its resistance to rifampicin.

In another specific case, the invention provides for a kit as described above, for the simultaneous detection of *M. leprae* and its resistance to rifampicin.

TABLE LEGENDS

Table 1 summarizes the nucleotide and amino acid chances (described by Telenti et al. (1993a and b), Kapur et al. 1994 and the present invention) in the rpoB gene fragment of rifampicin resistant *M. tuberculosis* isolates. Codon numbering is as in FIG. 1. New mutations described by the current invention are indicated with an asterisk (*).

Table 2 lists the sequences of the primers and probes selected from the rpoB gene.

2A: *M. tuberculosis*

2B: other mycobacterial species

Table 3 shows the hybridization results obtained with probe MT-POL-1, with DNA from different mycobacterial and non-mycobacterial species.

Table 4 shows some representative results obtained with LiPA for some *M. tuberculosis* isolates which have been sequenced and the interpretation of the different LiPA patterns.

Table 5 shows the occurrence of the different rpoB mutations in *M. tuberculosis* in different geographical areas. Abbreviations: Bel=Belium, Bengla=Bengladesh, Bur-Fa=Burkina faso, Buru=Burundi, Can=Canada, Chi=Chili, Col=Colombia, Egy=Egypt, Gui=Guinea, Hon=Honduras, Pak=Pakistan, Rwa=Rwanda, Tun=Tunesia.

Table 6 shows a comparison of LiPA results versus rifampicin resistance determination in culture for *M. tuberculosis*. S=Sensitive, R=Resistant.

FIGURE LEGENDS

FIG. 1 represents the nucleotide sequence and the amino acid sequence of the mutation region of respectively the rpoB gene and the RNA polymerase β-subunit of a wild-type (i.e. not resistant) *Mycobacterium tuberculosis* strain (ITG 9081). The codon (amino acid) numbering is as in Telenti et al. (1993a). The nucleotides or amino acids involved in resistance-inducing changes are underlined. The observed mutations are boxed. The horizontal bars indicate the positions of some of the oligonucleotide probes (one probe per group is indicated).

FIG. 2 shows the partial nucleotide sequence of the newly described rpoB mutant allele of *M. tuberculosis* strain ITG 9003 (SEQ ID NO 34).

FIG. 3 shows results obtained on LiPA-strips with probes S44 and S4444 applied at different concentrations on the membrane strip. As target material, nucleic acid preparations of *M. tuberculosis* strains ITG 8872 and ITG 9081 were used.

FIG. 4 gives a comparison of the performance of probes S44 and S4444 in a Line probe assay conformation. The probes on strip A and B are identical except for S44 and S4444. The hybridizations were performed using amplified material originating from *M. tuberculosis* strain ITG 8872.

FIG. 5 shows the partial nucleotide sequence of the presumptive rpoB gene of *M. paratuberculosis* strain 316F (SEQ ID NO 35)

FIG. 6 shows the partial nucleotide sequence of the presumptive rpoB gene of *M. aviuim* strain ITG 5887 (SEQ ID NO 36)

FIG. 7 shows the partial nucleotide sequence of the presumptive rpoB gene of *M. scrofulaceum* strain ITG 4979 (SEQ ID NO 37)

FIG. 8 shows the partial nucleotide sequence of the presumptive rpoB gene of *M. kansasii* strain ITG 4987 (SEQ ID NO 56)

Figure 9:
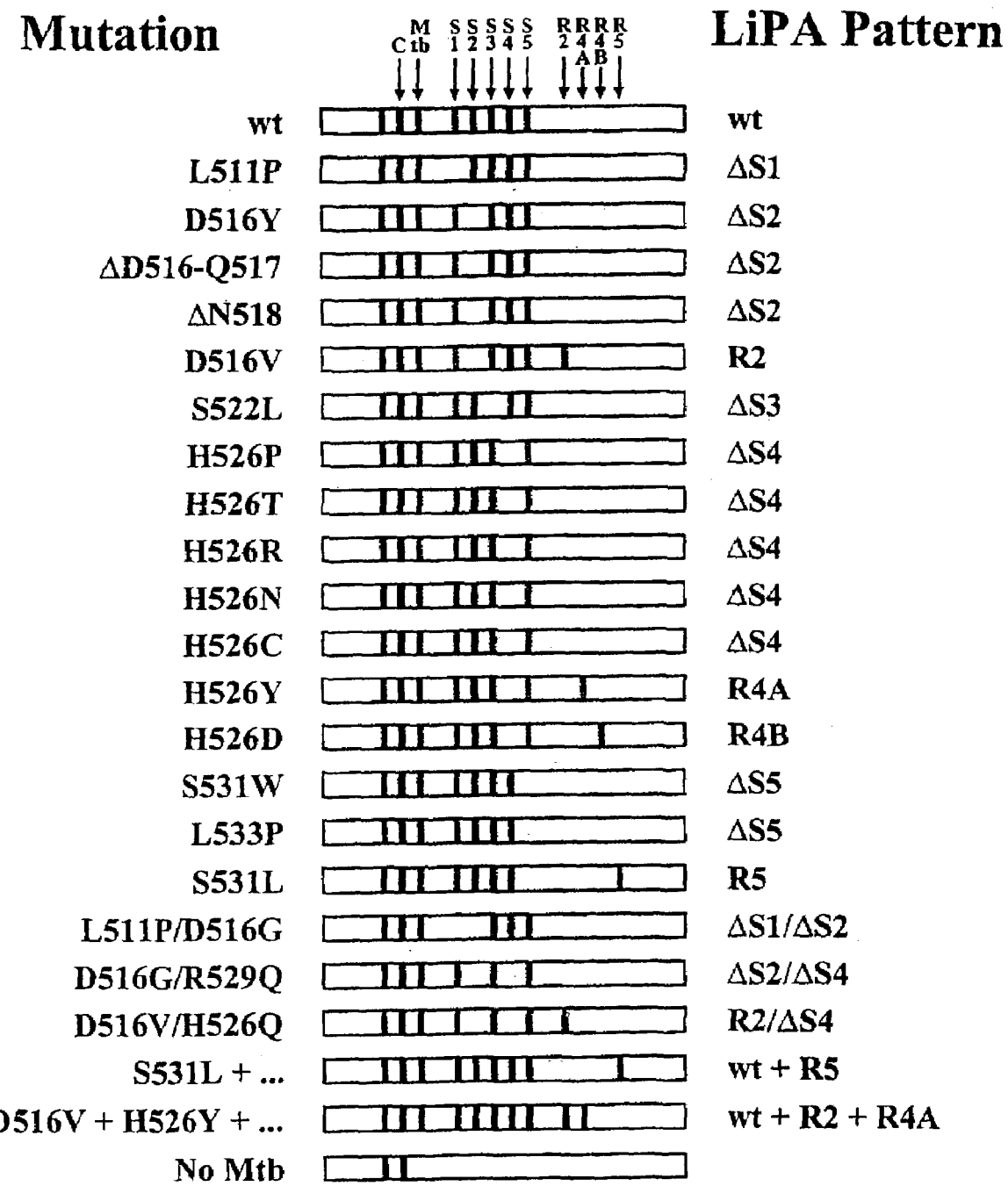

FIG. 9 shows some rpoB mutations in *M. tuberculosis* and their corresponding LiPA patterns. Nomenclature of the mutations is as described in Table 1. Nomenclature of the LiPA pattern is as follows:

wt=positive hybridization with all S-probes, and negative hybridization with all R-probes;

ΔS1-5=absence of hybridization with the respective S-probe;

R2, 4A, 4B, 5=positive hybridization with the respective R-probes and absence of hybridization with the corresponding S-probe;

C=positive control line: should be positive when the test is carried out properly;

Mtb=MT-POL-probe.

Only one probe of each group is mentioned, but it stands for the whole group: e.g. S5 stands for S5, S55, S555, S5555, S55C, S55M.

Figure 10:
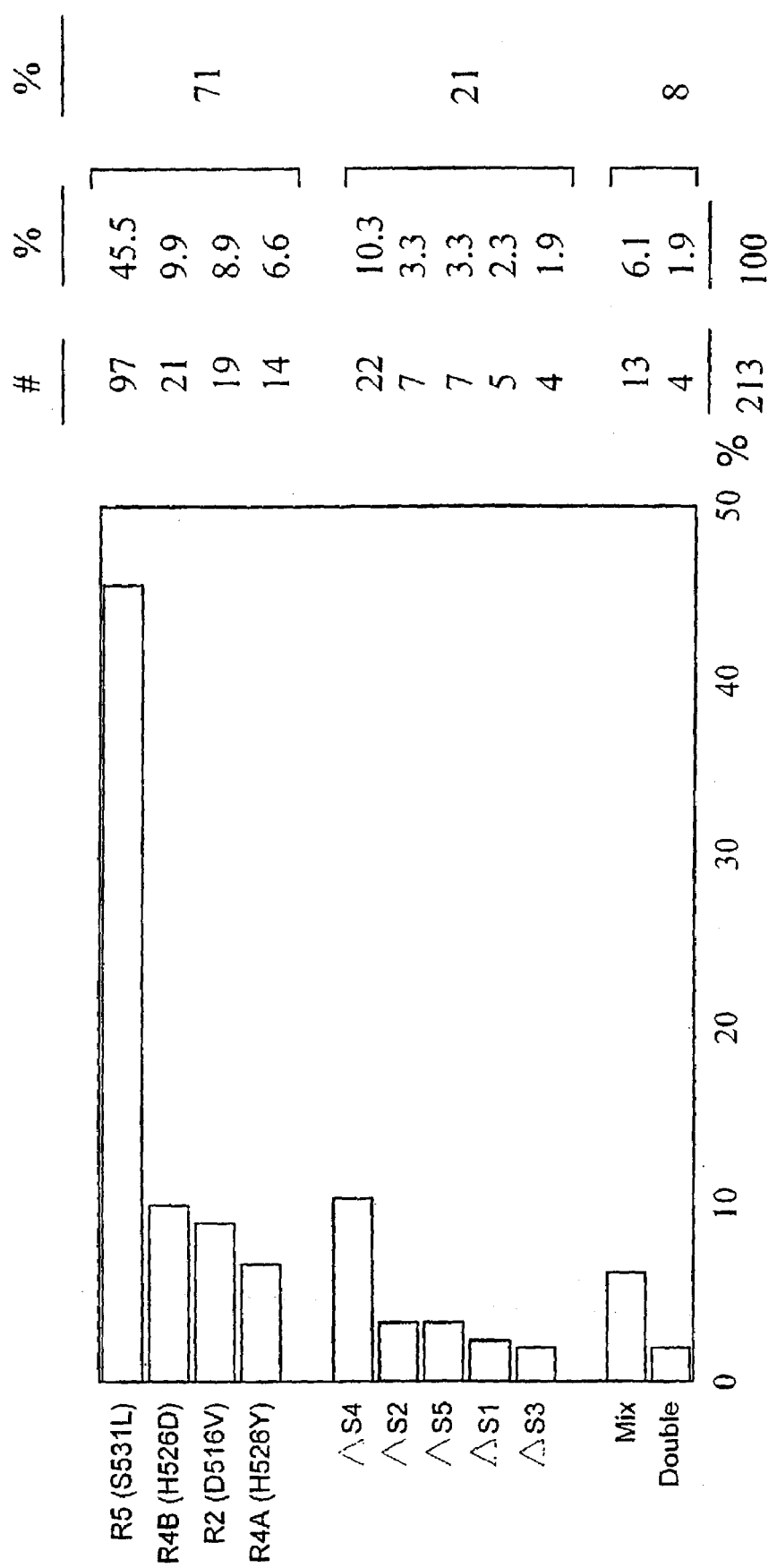

FIG. 10 shows the frequency of the different mutations encountered in the rifampicin-resistant *M. tuberculosis* strains analysed by LiPA. Nomenclature is as in FIG. 9. "Mix" means that a mix of strains was present in the sample. "Double" means the presence of two mutations in one strain.

FIG. 11 shows the partial nucleotide sequence of the presumptive rpoB gene of MAC strain ITG 926 (SEQ ID NO 69).

EXAMPLE 1

Amplification of the rpoB Gene Fragment in *M. tuberculosis*

After nucleic acid extraction from mycobacterial isolates (either cultured or present in body fluid or tissue) 2 μl product was used to amplify the relevant part of the rpo B gene by using one or more combinations between the 5'-primers (P1 (SEQ ID NO 30), P2, P3 (SEQ ID NO 31) and P7 (SEQ ID NO 41)) and the 3'-primers (P4 (SEQ ID NO 32). P5 (SEQ ID NO 33), P6 and P8 (SEQ ID NO 42).

The sequence of these primers is given in Table 2, P1, P3, P4, P5, P7 and P8 are new primer sequences, described by the current invention. P2 and P6 have been described before (Telenti et al. 1993a).

These primers may be labeled with a label of choice (e.g. biotine). Different primer-based target-amplification systems may be used. For amplification using the PCR, the conditions used are described hereafter. Single-round amplification with primers P1 and P5 involved 35 cycles of 45 sec/94° C., 45 sec/58° C. 45 sec/72° C. If a nested PCR was preferable, in the second round primers P3 and P4 were used and 25 cycles (45 sec/94° C. 60 sec/68° C.) were performed starting from 1 μl of first round product.

If P3 and P4 were used in a single-round PCR, the following cycling protocol was used: 30 cycles of 1 min/95° C., 1 min/55° C., 1 min/72° C. The same cycling protocol for set of primers P2/P6.

PCRs were usually performed in a total volume of 50 μl containing 50 mM KCl, 10 mM Tris-HCl (pH 8.3), 2.2 mM $MgCl_2$, 200 μl each dNTP, 0.01% gelatine and 1 U Taq polymerase.

Primer concentrations ranged between 10 and 25 pmol/reaction.

Since the set of primers P3/P4 yielded significantly stronger signals after hybridization than the set of primers P2/P6, the first set of primers was used for all further hybridization experiments. Set of primers P2/P6 was used for sequence analysis. Nested PCR using P2 and P6 as outer primers and P3 and P4 as inner (biotinylated) primers was only used for direct detection in clinical samples (expectorations and biopsies).

The length of the amplified product, as monitored by agarose-gelelectrophoresis, is as follows:

Primer set P1/P5: 379 basepairs
Primer set P3/P4: 257 basepairs
Primer set P2/P6: 411 basepairs
Primer set P7/P8: 339 basepairs

EXAMPLE 2

Sequencing of rpoB Gene Fragments from *M. tuberculosis* Strains

DNA extracted from mycobacterial isolates known to be resistant or sensitive to rifampicin was amplified using the set of primers P2/P6 (of which P6 was biotinylated at the 5' end). Direct sequencing of single stranded PCR-product was performed by using streptavidin coated beads and the Taq Dye Deoxy Terminator/Cycle Sequencing kit on an AB1373A DNA sequencer (Applied Biosystems, Forster City, Calif. USA) as recommended by the manufacturer. The primers used for sequencing were the same than those used for amplification (P2 or P6).

As expected, all sensitive (=sensitive in culture and sensitive LiPA pattern) strains sequenced (7) yielded a wild-type sequence (no mutation). In most resistant strains a mutation could be identified. Most of these mutations have been previously described (Telenti et al. 1993a, 1993b, Kapur et al. 1994). However, 4 new mutations are described in the current invention: D516G, H526C, H526T and R529Q (see also Table 1 (*)). The full sequence of the amplified rpoB fragment of mutant allele H526C (isolate ITG 9003) is shown in FIG. 2 (SEQ ID NO 34) by way of an example.

A few strains (3/180, see table 6) were resistant to rifampicin in culture but showed a wild-type LiPA pattern. After sequencing, these isolates all showed a wild-type rpoB gene sequence, confirming the hybridization results. It is therefore possible that for these isolates a different molecular mechanism of rifampicin resistance applies.

EXAMPLE 3

Development of the Line Probe Assay (LiPA)-Strip

The principle and protocol of the line probe assay was as described earlier (Stuyver et al. 1993) with a few exceptions. Instead of the incorporation of biotinylated dUTP, biotinylated primers were used and the hybridization and stringent wash were performed at 50° C. in 3×SSC/20% deionized formamide.

The mutations in the rpoB gene leading to resistance to rifampicin are mainly located in a small area of the gene spanning 67 nucleotides (23 amino acid codons). At least 17 nucleotides, evenly interspersed over this region, are involved in mutations leading to at least 28 different amino acid changes. Such a complexity of nucleotide changes poses problems for the detection of all these changes in a single hybridization step. In principle, per mutated site one wild-type probe would be needed and per nucleotide change one mutant-probe specifically detecting that particular mutation. Hence, a hybridization test would involve at least about 35 sequence specific oligonucleotide probes which would render this test complex to manufacture and use, and consequently commercially less attractive.

Figure 1:
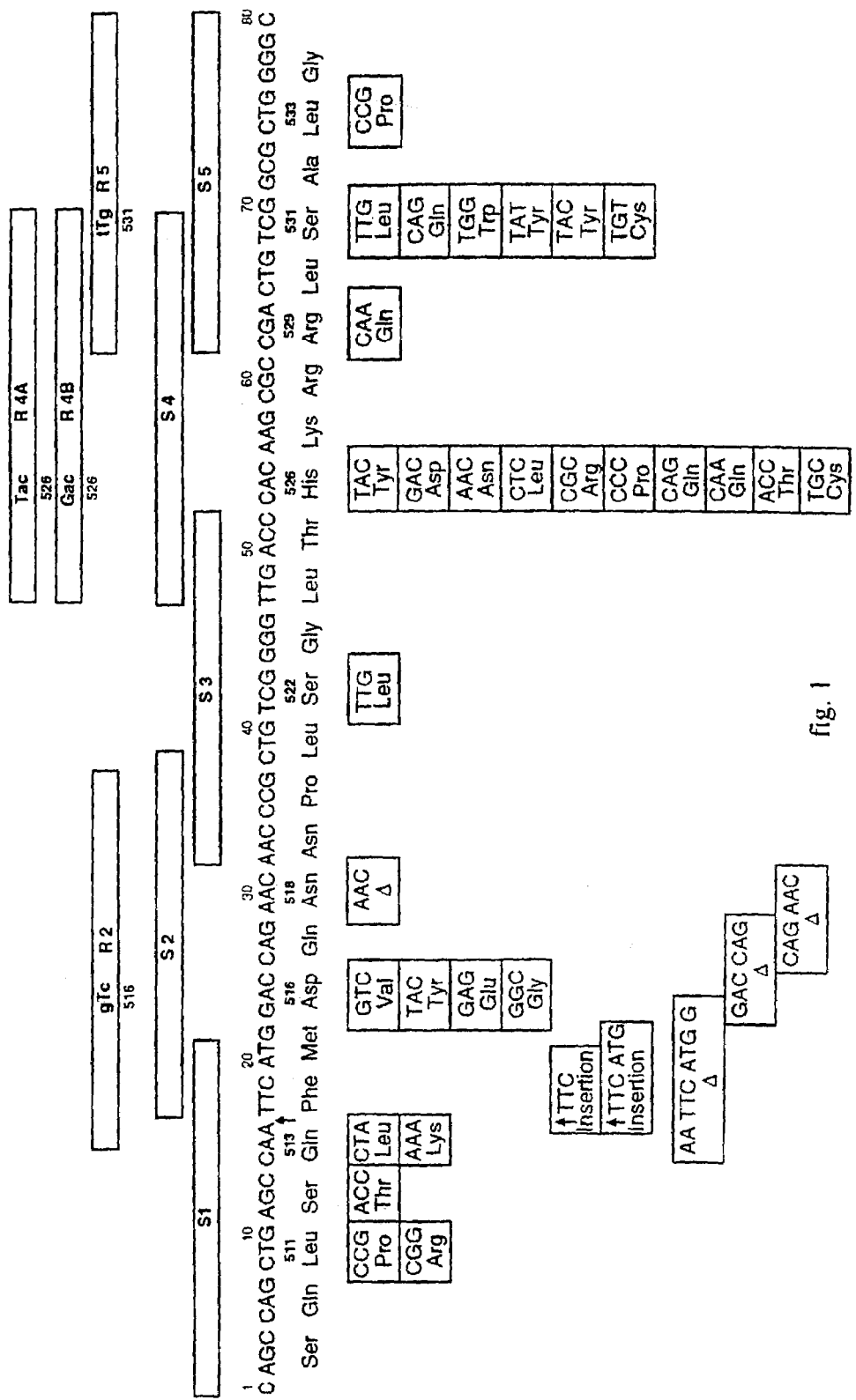

Therefore a particular approach was designed making use of carefully chosen wild-type (S-) probes, each spanning more than one polymorphic site and overlapping the complete area of relevance (see FIG. 1). Doing so, the set of at least 10 wild-type probes could be reduced to a total of five or six probes. These probes were meticulously adjusted experimentally such that the presence of each resistance causing mutation in the rpoB mutation region resulted in a clearly detectable decrease in hybrid-stability between the target and at least one of these probes under the same hybridization and wash conditions.

Since with this combination of probes all relevant mutations described so far can be detected, rifampicin resistance can be monitored in *Mycobacterium tuberculosis* isolates. This set of probes is also able to detect the presence of non-described mutations, e.g. the TGC mutation at position 526 in strain ITG 9003.

Although strictly taken the addition of mutant (R-) probes to the selected panel of wild-type probes is obsolete, for scientific purposes it might be informative to detect the exact point mutation present. Therefore, 4 mutant probes (R2, R4A, R4B, R5) were designed which correspond to the most frequently occurring mutations and which, taken together, are able to positively identify more than 70% of all resistant cases (see FIG. 10). Additional mutant probes (e.g. R1, R2B, R2C, R3, R4C, R4D, R4E, R5B, R5C) may be added to this set of 4 in order to positively identify most clinically relevant resistant cases. The addition of these probes also adds to the reliability of the assay since the appearance of a mutant probe should inevitably result in the disappearance of a wild-type probe if one is not dealing with mixed infections. In some cases, it may be of clinical relevance to distinguish between the different mutations possibly present. This situation may occur for instance at amino-acid position 516. If at that position the normal (wild-type) amino acid present (Aspartic acid), changes into a Valine or Tyrosine, high level resistance or intermediate level resistance to rifampicin is induced; however, unpublished data seem to indicate that the sensitivity to rifabutin is maintained. Hence, for infections by strains with this mutation, rifabutin would still be effective where as rifampicin is not. The same may be true for codon 511 but, to our knowledge, these are the only mutation-sites for which the effect of rifampicin and rifabutin might be different; usually strains resistant to rifampicin are also resistant to rifabutin.

In order to develop a LiPA-strip to detect the presence of mutations generating resistance to rifampicin (and/or rifabutin) in *M. tuberculosis* a total of 36 oligonucleotide probes were synthesized and evaluated in a reverse hybridization test. The sequence of these probes is shown in Table 2A (wild-type and mutation probes). The first set of probes tested was: S1, S2, S3, S4, S5, R2, R4A, R4B and R5. Under the conditions used for reverse hybridization most probes did not perform as theoretically expected and modifications had to be introduced leading to the synthesis and evaluation of the following additional probes: S11, S33, S44, S4444, S5555, R44A, R444A, R44B, R444B, R55. From the total panel of probes, probes exhibiting the most optimal features with respect to specificity and sensitivity, under the same experimental conditions were selected for further use.

The prefered probes with wild-type sequences (S-probes) which together overlap the entire rpoB region of interest are: S11, S2, S33, S4444 and S55 or S5555 (see Table 2). Resistance will be detected by a loss of hybridization signal with any of these S-probes.

The prefered mutation probes (R-probes) are: R2, R444A, R444B and R55 (see table 2). In some cases of resistance a loss of hybridization signal with the S-probes may be accompanied by a positive hybridization signal with the corresponding R-probe.

By way of an example, some of the rpoB-mutations and their corresponding LiPA pattern are shown in FIG. 9.

Although the probes from the same group (e.g. probes S4, S44, S444 and S4444) are differing only slightly from each other, their hybridization characteristics may vary considerably. This is illustrated by way of example in an experiment in which the performance of probes S44 and S4444 is compared using PCR products originating from two *M. tuberculosis* strains (ITG 8872 and ITG 9081) both displaying a wild-type sequence in the target region of probes S44 and S4444. The difference between both probes is shown below

```
S44      GGTTGACCCACAAGCGCCGA
         ||||||||||||||||||||
S4444        TTGACCCACAAGCGCCGACTGTC
```

Probe S44 was chosen on a theoretical basis from the known gene sequence (Telenti et al. 1993a). This probe would be theoretically the best probe for discriminating mismatches in the CAC-codon (underlined) since this codon is in the central part of the probe. However, in contrast to the general rules, the performance of probe S4444 proved to be significantly better (as described in the following experiment).

Both probes were applied to nitrocellulose strips in different amounts (2.4, 1.2 and 0.6 pmol/strip). After fixation and blocking of the strips, the probes were hybridized with biotinylated PCR fragments (from strains IGT 8872 and ITG 9081) as described earlier. The results are shown in FIG. 3.

Under the hybridization conditions used (3×SSC. 20% deionized formamide. 50° C.) the signals obtained with probe S44 are very weak. On the other hand probe S4444 generates very strong and reliable signals. Consequently, probe S4444 is prefered over S44 for use on the LiPA-strip. This dramatic effect cannot only be attributed to the difference in length of both probes, but also the location seems to be of importance. Most probably the secundary structure of the target region of the probes highly influences the hybridization characteristics.

In FIG. 4 the results of another experiment are shown in which the performance of both probes is compared in the context of the other probes. Both strips A and B are identically processed using amplified product originating from strain ITG 8872. Both strips are almost identical except that strip A contains probe S44 (0.6 pmol) and strip B probe S4444 (0.1 pmol) and the order of the probes applied to the strip is different. On strip A probe S44 is negative whereas on strip B probe S4444 is clearly positive, although in both cases there is a perfect match between the target and the probe and in both cases a positive result would have been expected.

These results clearly illustrate that probe design, especially under the fixed conditions of the reverse hybridization format (the same conditions for each probe) is not straightforward and probes have to be evaluated meticulously before they can be used in a reverse hybridization format.

In general we can state that suitable probes cannot always be simply derived on a theoretical basis from a known gene sequence.

Although not detected among the isolates tested in the current invention, the presence of a silent mutation may give rise to a resistant pattern on the strips (one wild-type probe missing) while the strain is sensitive. Up to now only one silent substitution has been described (in codon 528: CGC→CGT: Telenti et al. 1993a). This mutation would result in a destabilization of the hybrid with probe S-4444. However, by adding to the strip a probe specific for hie silent mutation (Probe SIL-1, Table 2), this silent mutation can be discriminated from resistance inducing mutations and would prevent misinterpretation of the pattern observed. Moreover, the SIL-probes can be applied on the strip at the same location than the corresponding S-probes (mixed probes). Doing so, no loss of hybridisation signal would be observed as a result of the silent mutation.

In order to detect the insertion mutations conferring rifampicin resistance, 514insF and 514insFM (see FIG. 1), two new wild-type probes were designed. S6 and S66, the sequence of which is represented in Table 2. Hybridization with nucleic acids originating from strains harbouring these insertion mutations, results in the absence of a hybridization signal with S6 and S66 (see also Table 1).

In order to positively identify more mutations than those detected by the set of R2, R4A, R4B and R5, a number of additional R-probes were designed, which may be added to the LiPA strip, using the same hybridization and wash conditions. Together with the above-described R-probes, the additional R-probes (R1, R2B, R2C, R3, R4C, R4D, R4E, R5B, R5C) allow a positive identification of the mutations most frequently encountered in the strain collection tested in the current application.

EXAMPLE 4

Probe Specific for the *M. tuberculosis* Complex

A line probe assay was developed in order to enable the simultaneous detection of the mutations causing resistance to rifampicin directly coupled to detection of the pathogen in casu *M. tuberculosis*.

Since it is extremely advantageous to be able to detect simultaneously the presence of *M. tuberculosis* and the presence or absence of a gene or mutation causing drug-resistance, the aim was to develop a *M. tuberculosis* probe contained in the same PCR fragment as at least one of the relevant resistance markers to be identified. Therefore rpoB genes of non-*M. tuberculosis* isolates were sequenced. These organisms were: *M. paratuberculosis* 316F. *M. avium* ITG5887, *M. scrofulaceum* ITG4979 and *M. kansasii* ITG4987. The sequences of the corresponding rpoB gene fragments are shown in FIGS. 5 to 8, respectively. In addition, the sequence of the rpoB gene fragments of *M. leprae* and *M. intracellulare* were known from the literature (Honoré and Cole. 1993; Guerrero et al. 1994). Comparison of these sequences with the rpoB gene sequence of *M. tuberculosis* enabled the delineation of a specific region (outside the region responsible for resistance) in the rpoB gene fragment from which the development of probes, potentially specific for *M. tuberculosis* appeared feasible. An oligonucleotide probe (further referred to as MT-POL-1) derived from that region with the following sequence:

GGA CGT GGA GGC GAT CAC ACC            (SEQ ID NO 23)

was further evaluated with respect to its sensitivity and specificity by hybridization on LiPA strips. The amplification and hybridization conditions were as described above. The results are summarized in Table 3. In addition to the four *M. tuberculosis* strains listed in Table 3, 521 more *M. tuberculosis* clinical isolates were tested: all isolates gave a positive hybridization signal. Evidently, also *M. bovis* strains hybridize with the probe, but it is clinically not relevant to distinguish *M. tuberculosis* from *M. bovis* for this purpose. In fact, throughout the application the term "*M. tuberculosis*" can be replaced by "*M. tuberculosis* complex", referring to *M. tuberculosis* s.s., *M. bovis*, *M. africanum* and *M. microti*, without affecting the significance of the results.

Although, using the sets of primers described in example 1, a PCR product may be obtained with DNA of some other *Mycobacterium* species and even some genetically unrelated micro-organisms which might also be present in the respiratory tract, none of these bacteria showed hybridization with the selected MT-POL-1 probe. In conclusion we can state that the selected probe is highly specific for *M. tuberculosis* complex strains and 100% sensitive for *M. tuberculosis*. Also other probes from this region might be useful for the specific detection of *M. tuberculosis* complex strains, such as: MT-POL-2, MT-POL-3, MT-POL-4 and MT-POL-5 (see Table 2).

In a similar way, the following probes can be used to differentiate *M. avium, M. paratuberculosis, M. scrofulaceum, M. kansasii, M. intracellulare* and *M. leprae* strains from each other and from other mycobacteria MA-POL-1, MP-POL-1, MS-POL-1, MK-POL-1, MI-POL-1 and ML-POL-1 respectively (see table 2B).

EXAMPLE 5

Evaluation of LiPA Strips for *M. tuberculosis*

LiPA strips were prepared carrying the following probes (in addition to a positive control line): MT-POL-1, S11, S2, S33, S4444, S5555, R2, R444A, R444B, R55.

These strips were hybridized with PCR products from *M. tuberculosis* strains for which the relevant rpoB gene sequence was determined.

Some representative results are summarized in Table 4.

The hybridization results completely correlated with the sequencing results, indicating that the probes used can discriminate at the level of a single mismatch. Each mutation screened for could be detected either by the absence of one of the wild-type probes (S-probes) or by the absence of a wild-type probe together with the presence of the corresponding mutant probe (R-probe). In the latter case, the exact mutation present can be derived from the hybridization results. However, the knowledge of the exact mutation present is not necessary to determine whether or not one is dealing with a strain resistant to rifampicin since each mutation screened for confers resistance. Sensitive strains, i.e. strains without mutations in the relevant part of the rpoB gene, give positive reactions on all S-probes while all R-probes score negative (=wt-pattern).

EXAMPLE 6

Direct Detection of *M. tuberculosis* Strains and Rifampicin-Resistance in Clinical Samples Sixty-eight clinical specimens from different geographical origins (13 and 35 sputum specimens from Belgium and Rwanda respectively, and 20 lymph node biopsies from Burundi) all positive in culture for *M. tuberculosis* and kept at −20° C. were analyzed. Sample preparation for amplification was based on the procedure of Boom et al. (1990) modified by De Beenhouwer et al. (submitted). A nested PCR approach for the relevant region of the rpoB gene was carried out with biotinylated inner primers (P3 and P4). After thermal cycling, the amplified product was incubated with the LiPA strip. Rifampicin resistance was determined on Löwenstein-Jensen using the proportion method of Canetti et al. (1963). For resistant strains, the MIC (Minimal Inhibitory Concentration) of rifampicin was determined on 7H10 agar (Heifets, 1988).

Microscopically, 20 (29.4%) samples were negative, 15 (22.1%) weakly positive (1+ or less according to the scale of the American Thoracic Society) and 33 (48.5%) strongly positive (≧+2) upon Ziehl-Neelsen staining.

The LiPA detected rifampicin sensitivity in 49 specimens (only *M. tuberculosis* and wild-type probes positive) and resistance in 19 specimens (*M. tuberculosis* probe positive, one of the wild-type probes missing, and eventually one of the mutation probes positive). In vitro rifampicin susceptibility testing confirmed these results with three exceptions. For all the sensitive strains, a sensitive probe pattern was observed indicating that possible silent mutations were not detected in this series. All strains displaying a resistance pattern were found to be resistant by conventional techniques. For three specimens (from three multidrug resistant patients from Rwanda) a sensitive pattern was obtained by PCR-LiPA while culture revealed resistance (MIC>2 μg/ml on 7H10). Sequencing of the rpoB region of these strains confirmed the wild-type gene sequence, possibly implying a different mechanism of rifampicin resistance in these cases or a mutation in another part of the rpoB-gene. It is also interesting to note that the nested PCR system gave positive results for all the tested specimens positive in culture including 20 Ziehl-Neelsen negative specimens. In another experiment (data not shown) including 17 smear negative sputum specimens from clinically suspected tuberculosis cases negative in culture, no signal at all was obtained with the LiPA system, indicating that the infections were most probably not caused by *M. tuberculosis*.

In a subsequent experiment, a large collection of clinical specimens from different geographical origin were tested in LiPA. Results are shown in Table 5. Of the 137 resistant strains found, quite a large number could be attributed to one of the mutations represented by the R-probes (R2, R4A, R4B, R5). Interestingly, some mutations seem to be more frequent in some countries as compared to others (e.g. in Tunesia and Egypt; R4B (=H526D), in Rwanda; R5 (S531L)). This mast eventually lead to different test formats for different countries.

On a total of 213 rifampicin-resistant strains analysed by LiPA in the current application, 151 (71%) could be attributed to the mutations S531L, H526D, D516V or H526Y, and were thus detectable by a positive signal with respectively probes R5, R4B, R2 and R4A (see FIG. 10).

On a total of 180 strains analysed both by culture and by LiPA, correct identification (sensitive/resistant) was made in 164 (=91.1%) of the strains (see Table 6). In three resistant strains. LiPA results and sequencing showed a wild-type rpoB-gene fragment, which indicates that the mechanism for rifampicin resistance could not be attributed to mutations in the investigated part of the rpoB gene.

Thirteen of the 180 analyzed strains were resistant in LiPA but seemed to be sensitive in culture. However, after reculturing 2 of these 13 strains in synthetic 7H11 medium in stead of the traditional Löwenstein Jensen medium, they turned out to be rifampicin resistant anyway. This uptil now unpublished finding shows that the conventional Löwenstein Jensen medium is not recommended for determination of antibiotic susceptibility of mycobacteria (possibly due to the presence of traces of antibiotics found in commercially available eggs used to prepare Löwenstein Jensen medium). Therefore, the percentage of discrepant strains which are resistant in LiPA but sensitive in culture (in this case 13/180=7.2%) is expected to be much lower (and possibly 0%) when culturing is done on a synthetic medium like 7H11.

Interestingly, most of the rifampicin resistant isolates (>90%) examined in the current application were in addition resistant to isoniazid, and thus multidrug-resistant (definition of multidrug resistance=resistant to at least isoniazid and rifampicin). Rifampicin resistance can thus be considered as a potential marker for multidrug resistance, and the above-described LiPA test may therefore be an important tool for the control of multidrug resistant tuberculosis.

In conclusion, the above-described method permits correct identification of *M. tuberculosis* and simultaneous detection of rifampicin resistance directly in clinical specimens without preculturing. It enables easy detection of rifampicin resistance directly in a clinical specimen in less than 24 hours.

EXAMPLE 7

Detection of Rifampicin Resistance in *M. leprae*

The above-described detection approach can also be applied to the detection of *M. leprae* present in biological samples coupled to the detection of its resistance to rifampicin. The sequence of the rpoB gene of *M. leprae* was described earlier by Honoré and Cole (1993). They only identified a limited number of mutations responsible for rifampicin resistance in *M. leprae*. It can be reasonably expected that, similar to *M. tuberculosis*, a lot of other mutations may cause rifampicin resistance in *M. leprae*, and that most of these mutations will be localized in a rather restricted area of the rpoB gene, corresponding to the "mutation region" described earlier in this application.

Therefore, a set of wild-type probes is selected overlapping the putative mutation region in the rpoB-gene of *M. leprae* (see table 2B):

| | |
|---|---|
| ML-S1 | (SEQ ID NO 58) |
| ML-S2 | (SEQ ID NO 59) |
| ML-S3 | (SEQ ID NO 60) |
| ML-S4 | (SEQ ID NO 61) |
| ML-S5 | (SEQ ID NO 62) |
| ML-S6. | (SEQ ID NO 63) |

Rifampicin resistance is revealed by an absence of hybridization with at least one of these ML-S probes. This set of ML-S probes will detect rifampicin-resistance causing mutations in this region, even though the sequence of these mutations has not yet been specified.

The above-mentioned ML-S probes have been carefully designed in such a way that they can all be used under the same hybridization and wash conditions. The same holds for the species specific ML-POL-1 probe, with which the ML-S probes can be combined to allow a simultaneous detection of *M. leprae* and its resistance to rifampicin.

All the probes mentioned in this example are contained in the same rpoB gene fragment of *M. leprae*, which can be obtained by PCR using a set of primers chosen from MGRPO-1 or MGRPO-2 (5' primers) and MGRPO-3 or MGRPO-4 (3' primers).

TABLE 1

| | Position | | Wild-type sequence | | | Mutation sequence | | | Probe detection | |
|---|---|---|---|---|---|---|---|---|---|---|
| Abbr. | Nucl. | Codon | Nucl. | Codon | AA | Nucl. | Codon | AA | Δ Wt probe | Mutant probe |
| L511P | 9 | 511 | T | CTG | Leu | C | CCG | Pro | S11 | — |
| L511R | 9 | 511 | T | CTG | Leu | G | CGG | Arg | S11 | — |
| S512T | 12 | 512 | G | AGC | Ser | C | ACC | Thr | S11 | — |
| Q513L | 15 | 513 | A | CAA | Gln | T | CTA | Leu | S11 | — |
| Q513K | 14 | 513 | C | CAA | Gln | A | AAA | Lys | S11 | — |
| 514 ins F | 16 | 514 | — | — | — | TTC | TTC | Phe | S6 | — |
| 514 ins FM | 16 | 514 | — | — | — | TTC ATG | TTC ATG | Phe Met | S6 | — |
| Δ514–516 | 15–23 | 514–516 | AA TTC ATG G | AA TTC ATG G | Gln Phe Met Asp | Δ | Δ | His | S1–S2–S6 | — |
| Δ516–517 | 23–28 | 516–517 | GAC CAG | GAC CAG | Asp Gln | Δ | Δ | Δ | S2–S6 | — |
| D516Y | 23 | 516 | G | GAC | Asp | T | TAC | Tyr | S2 | — |
| D516V | 24 | 516 | A | GAC | Asp | T | GTC | Val | S2 | R2 |
| D516E | 25 | 516 | C | GAC | Asp | G | GAG | Glu | S2 | — |
| D516G(*) | 24 | 516 | A | GAC | Asp | G | GGC | Gly | S2 | — |
| Δ517–518 | 26–31 | 517–518 | CAG AAC | CAG AAC | Gln Asn | Δ | Δ | Δ | S2 | — |
| Δ518 | 29–31 | 518 | AAC | AAC | Asn | Δ | Δ | Δ | S2 | — |
| S522L | 42 | 522 | C | TCG | Ser | T | TTG | Leu | S33 | — |
| H526Y | 53 | 526 | C | CAC | His | T | TAC | Tyr | S4444 | R444A |
| H526D | 53 | 526 | C | CAC | His | G | GAC | Asp | S4444 | R444B |
| H526N | 53 | 526 | C | CAC | His | A | AAC | Asn | S4444 | — |
| H526C(*) | 53–54 | 526 | CA | CAC | His | TG | TGC | Cys | S4444 | — |
| H526R | 54 | 526 | A | CAC | His | G | CGC | Arg | S4444 | — |
| H526P | 54 | 526 | A | CAC | His | C | CCC | Pro | S4444 | — |
| H526Q | 55 | 526 | C | CAC | His | $^A_G$ | CA$^A_G$ | Gln | S4444 | — |
| H526L | 54 | 526 | A | CAC | His | C | CTC | Leu | S4444 | — |
| H526T(*) | 53–54 | 526 | CA | CAC | His | AC | ACC | Thr | S4444 | — |
| R529Q(*) | 63 | 529 | G | CGC | Arg | A | CAA | Gln | S4444 | — |
| S531Q | 68–69 | 531 | TC | TCG | Ser | CA | CAG | Gln | S5555 | — |
| S531L | 69 | 531 | C | TCG | Ser | T | TTG | Leu | S5555 | R55 |

TABLE 1-continued

| Abbr. | Position Nucl. | Position Codon | Wild-type sequence Nucl. | Wild-type sequence Codon | Wild-type sequence AA | Mutation sequence Nucl. | Mutation sequence Codon | Mutation sequence AA | Probe detection Wt probe | Probe detection Mutant probe |
|---|---|---|---|---|---|---|---|---|---|---|
| S531W | 69 | 531 | C | TCG | Ser | G | TGG | Trp | S5555 | — |
| S531Y | 69–70 | 531 | CG | TCG | Ser | A<sup>T</sup>C | TA<sup>T</sup>C | Tyr | S5555 | — |
| S531C | 69–70 | 531 | CG | TCG | Ser | GT | TGT | Cys | S5555 | — |
| L533P | 75 | 533 | T | CTG | Leu | C | CCG | Pro | S5555 | — |

TABLE 2

Primers and probes selected from the rpoB gene

| | | SEQ ID NO |
|---|---|---|
| 2A: M. tuberculosis Primers | | |
| P1 | GAGAATTCGGTCGGCGAGCTGATCC | 30 |
| P2 | TACGGTCGGCGAGCTGATCC | |
| P3 | GGTCGGCATGTCGCGGATGG | 31 |
| P4 | GCACGTCGCGGACCTCCAGC | 32 |
| P5 | CGAAGCTTGACCCGCGCTACACC | 33 |
| P6 | TACGGCGTTTCGATGAACC | |
| P7 | CGGCATGTCGCGGATGGAGCG | 41 |
| P8 | CGGCTCGCTGTCGGTGTACGC | 42 |
| Probes species-specific probes | | |
| MT-POL-1 | GGACGTGGAGGCGATCACACC | 23 |
| MT-POL-2 | CGATCACACCGCAGACGTTGATC | 24 |
| MT-POL-3 | CATCCGGCCGGTGGTCGC | 25 |
| MT-POL-4 | CTGGGGCCCGGCGGTCT | 26 |
| MT-POL-5 | CGGTCTGTCACGTGAGCGTG | 27 |
| wild-type probes | | |
| S1 | CAGCCAGCTGAGCCAATTCATG | 1 |
| S11 | CAGCCAGCTGAGCCAATTCAT | 2 |
| S2 | TTCATGGACCAGAACAACCCGC | 3 |
| S3 | AACCCGCTGTCGGGGTTGA | 4 |
| S33 | AACCCGCTGTCGGGGTTGACC | 5 |
| S4 | GTTGACCCACAAGCGCCGA | 6 |
| S44 | GGTTGACCCACAAGCGCCGA | 7 |
| S444 | TTGACCCACAAGCGCCGACTGT | 43 |
| S4444 | TTGACCCACAAGCGCCGACTGTC | 8 |
| S5 | GACTGTCGGCGCTGGGG | 9 |
| S55 | CGACTGTCGGCGCTGGGGC | 10 |
| S555 | GACTGTCGGCGCTGGGGCC | 39 |
| S5555 | GACTGTCGGCGCTGGGGC | 40 |
| S55C | GCCCCAGCGCCGACAGTCG | 44 |
| S55M | CGACTGTCGGCGTTGGGGC | 45 |
| S6 | TGAGCCAATTCATGGACCAGAA | 11 |
| S66 | CTGAGCCAATTCATGGACCAGA | 12 |
| SIL-1 | CCACAAGCGTCGACTGTCG | 13 |
| mutant probes | | |
| R2 | AATTCATGGTCCAGAACAACCCG | 14 |
| R4A | GGTTGACCTACAAGCGCCGA | 15 |
| R44A | GGGTTGACCTACAAGCGCCGA | 16 |
| R444A | TTGACCTACAAGCGCCGACTGTC | 17 |
| R4B | GTTGACCGACAAGCGCCGA | 18 |
| R44B | GGTTGACCGACAAGCGCCGA | 19 |
| R444B | TTGACCGACAAGCGCCGACTGTC | 20 |
| R5 | CGACTGTTGGCGCTGGGG | 21 |
| R55 | CGACTGTTGGCGCTGGGGC | 22 |
| R1 | CAGCCAGCCGAGCCAATTCAT | 46 |
| R2B | AATTCATGTACCAGAACAACCCG | 47 |
| R2C | ATGGACCAGAACCCGCTGTCG | 48 |
| R3 | AACCCGCTGTTGGGGTTGACC | 49 |
| R4C | TTGACCCGCAAGCGCCGACTGTC | 50 |
| R4D | TTGACCCCCAAGCGCCGACTGTC | 51 |
| R4E | TTGACCTGCAAGCGCCGACTGTG | 52 |
| R5B | CGACTGTGGGCGCTGGGGC | 53 |
| R5C | ACTGTGGGCGGCGGGGCCC | 54 |
| 2B: other mycobacterial species primers | | |
| MGRPO-1 | CCAAAACCAGATCCGGGTCGG | 64 |
| MGRPO-2 | GTCCGGGAGCGGATGACCAC | 65 |
| MGRPO-3 | GGGTGCACGTCGCGGACCTC | 66 |

TABLE 2-continued

Primers and probes selected from the rpoB gene

| | | SEQ ID NO |
|---|---|---|
| MGRPO-4 | GGGCACATCCGGCCGTAGTG | 67 | probes

| | | |
|---|---|---|
| MP-POL-1 | CATCCGTCCCGTCGTGGC | 28 |
| MA-POL-1 | CATCCGTCCAGTCGTGGCG | 29 |
| MS-POL-1 | GCCGGTCGTGGCCGCG | 38 |
| MK-POL-1 | AGCGCCGGCTTTCGGCGC | 55 |
| ML-POL-1 | GACGCTGATCAATATCCGTCCGG | 57 |
| MI-POL-1 | ATCCGGCCGGTCGTCGCC | 68 |
| ML-S1: | CAGCCAGCTGTCGCAGTTCATG | 58 |
| ML-S2: | GTTCATGGATCAGAACAACCCTC | 59 |
| ML-S3: | AACCCTCTGTGGGGCCTGACC | 60 |
| ML-S4: | ACCCAGAAGCGCCGGCTGTC | 61 |
| ML-S5: | GGCTGTCGGCGCTGGGC | 62 |
| ML-S6: | CTGTCGCAGTTCATGGATCAGA | 63 |

TABLE 3

Hybridization results obtained with probe MT-POL-1

| | Species | Strain | MT-POL-1 |
|---|---|---|---|
| 1 | M. tuberculosis | ATCC 27294 | + |
| 2 | M. tuberculosis | NCTC 7417 | + |
| 3 | M. tuberculosis | ITG 8017 | + |
| 4 | M. tuberculosis | ITG 9173 | + |
| 5 | M. bovis | BCG (Kopen) | + |
| 6 | M. bovis | patient isolate | + |
| 7 | M. avium | ITG 5872 | − |
| 8 | M. avium | ITG 5874 | − |
| 9 | M. intracellulare | ITG 5913 | − |
| 10 | M. intracellulare | ITG 5918 | − |
| 11 | M. paratuberculosis | 2 E | − |
| 12 | M. kansasii | ITG 4987 | − |
| 13 | M. marinum | ITG 7732 | − |
| 14 | M. scrofulaceum | ITG 4988 | − |
| 15 | M. gordonae | ITG 4989 | − |
| 16 | Bordetella pertussis | NCTC 8189 | − |
| 17 | Bordetella parapertussis | NCTC 7385 | − |
| 18 | Bordetella bronchiseptica | NCTC 8761 | − |
| 19 | Moraxella catarrhalis | LMG 5128 | − |
| 20 | Moraxella catarrhalis | LMG 1133 | − |
| 21 | Moraxella catarrhalis | LMG 4200 | − |
| 22 | Moraxella catarrhalis | LMG 4822 | − |
| 23 | Haemophilus inhluenzae | NCTC 8143 | − |
| 24 | Haemophilus intluenzae | ITG 3877 | − |
| 25 | Streptococcus pneumoniae | H90-11921 | − |
| 26 | Streptococcus pneumoniae | H91-04493 | − |
| 27 | Streptococcus pneumoniae | H90-11780 | − |
| 28 | Pseudomonas cepacia | ATCC 25609 | − |
| 29 | Acinetobacter calcoaceticus | ATCC 23055 | − |
| 30 | Staphylococcus aureus | 6420 | − |
| 31 | Staphylococcus aureus | 6360 | − |
| 32 | Pseudomonas aeruginosa | 5682 | − |
| 33 | Pseudomonas aeruginosa | 5732 | − |

TABLE 4

Interpretation of LiPA-results for rifampicin resistance detection in M. tuberculosis

| MT-POL-1 | S11 | S2 | S33 | S4444 | S55 | R2 | R444A | R444B | R55 | LiPA pattern | Mutation (verified by sequencing) | Interpretation |
|---|---|---|---|---|---|---|---|---|---|---|---|---|
| + | + | + | + | + | + | − | − | − | − | wt | − | Sensitive |
| + | − | + | + | + | + | − | − | − | − | ΔS1 | in S1 | Resistant |
| + | + | − | + | + | + | − | − | − | − | ΔS2 | in S2 | Resistant |
| + | + | − | + | + | + | + | − | − | − | R2 | D516V | Resistant |
| + | + | + | − | + | + | − | − | − | − | ΔS3 | in S3 | Resistant |
| + | + | + | + | − | + | − | − | − | − | ΔS4 | in S4 | Resistant |
| + | + | + | + | − | + | − | + | − | − | R4A | II526Y | Resistant |
| + | + | + | + | − | + | − | − | + | − | R4B | II526D | Resistant |
| + | + | + | + | + | − | − | − | − | − | ΔS5 | in S5 | Resistant |
| + | + | + | + | + | − | − | − | − | + | R5 | S531L | Resistant |

TABLE 5

Occurrence of different mutations in M. tuberculosis strains originating from different countries

| # | Mutation | Bel | Bengla | Benin | Bur-Fa | Buru | Can | Chi | Col | Egy | Gui | Hon | Pak | Rwa | Tun |
|---|---|---|---|---|---|---|---|---|---|---|---|---|---|---|---|
| 2 | ΔS1 | | 1 | | | | | | | | | | | | 1 |
| 2 | ΔS2 | | 1 | | | | | | | | | | | 1 | |
| 4 | ΔS3 | 1 | | 3 | | | | | | | | | | | |
| 19 | ΔS4 | 1 | 1 | | 2 | 2 | 1 | 1 | | | | 1 | 8 | 2 | |
| 8 | ΔS5 | | 1 | | | 1 | | | 2 | | 1 | 2 | 1 | | |
| 11 | R2 | 2 | | | | | 1 | | | | 2 | | | 6 | |

TABLE 5-continued

Occurrence of different mutations in *M. tuberculosis* strains originating from different countries

| # | Mutation | Bel | Bengla | Benin | Bur-Fa | Buru | Can | Chi | Col | Egy | Gui | Hon | Pak | Rwa | Tun |
|---|---|---|---|---|---|---|---|---|---|---|---|---|---|---|---|
| 15 | R4a | 4 | 1 | 1 | 2 | | | | | 2 | | | 1 | 2 | 2 |
| 14 | R4b | | | | 1 | | | 1 | | 3 | | | | 1 | 8 |
| 56 | R5 | 9 | 1 | | | | 1 | 1 | 1 | | 1 | | 6 | 26 | 10 |
| 1 | R2 + ? | | | | | | | | | | | | | | 1 |
| 2 | R4a + R5 | | | | | | | | | | | | 1 | | 1 |
| 1 | R4b + R5 | | | | | | | | | | | | | 1 | |
| 1 | ΔS1/R2 | | | | | | | | | | | | | | 1 |
| 1 | ΔS1/ΔS2 | | | | | | | | 1 | | | | | | |
| 137 | Totaal | 17 | 6 | 1 | 6 | 0 | 3 | 6 | 3 | 6 | 3 | 0 | 12 | 41 | 33 |

TABLE 6

Comparison of LiPA results versus rifampicin resistance determination in culture for *M. tuberculosis*.

| | | Culture | |
|---|---|---|---|
| | | S | R |
| LiPA | S | 71 | 3 |
| | R | 13 | 93 |

REFERENCES

Asseline J. Delarue M. Lancelot G. Toulme F. Thuong N (1984) Nucleic acid-binding molecules with high affinity and base sequence specificity: intercalating agents covalently linked to oligodeoxynucleotides Proc. Natl. Acad. Sci. USA 81(11):3297-301.

Banerjee A., Dubnau E. Quernard A. et al. inhA, a gene encoding a target for Isoniazid and Ethionamide in *Mycobacterium tuberculosis*. Science 1994: 263: 227-30.

Barany F. Genetic disease detection and DNA amplification using cloned thermostable ligase. Proc Natl Acad Sci USA 1991: 88: 189-193.

Bej A, Mahbubani M. Miller R. Di Cesare J. Haff L. Atlas R. Mutiplex PCR amplification and immobilized capture probes for detection of bacterial pathogens and indicators in water. Mol Cell Probes 1990: 4:353-365.

Boom R., Sol C. J. A., Salimans M. M. M. et al. Rapid and simple method for purification of nucleic acids. J Clin Microbiol 1990: 28: 495-503.

Canetti G. Froman S., Grosset J. et al. Mycobacteria: laboratory methods for testing drug sensivity and resistance. Bull WHO 1963: 29: 565-79.

Claridge J. E., Sliawar R. M., Shinnick T. M. and Plikaytis B. B. Large-scale use of polymerase schain reaction for detection of *Mycobacterium tuberculosis* in a routine mycobacteriology laboratory. J Clin Microbiol 1993; 31: 2049-56.

Compton J. Nucleic acid sequence-based amplification. Nature 1991: 350: 91-92.

Culliton B. Drug resistant Th may bring epidemic. Nature 1992: 356: 473.

Douglas J. Steyn L. M. A ribosomal gene mutation in streptomycin-resistant *Mycobacterium tuberculosis* isolates. J. Infect. Dis. 1993: 167: 1505-1506.

Duck P. Probe amplifier system based on chimeric cycling oligonucleotides. Biotechniques 1990; 9: 142-147.

Finken M., Kirschner P., Meier A. Wrede A. and Böttger E. Molecular basis of streptomycin resistance in *Mycobacterium tuberculosis*: Alternations of the ribosomal protein S12 gene and point mutations within a functional 16S ribosomal RNA pseudoknot. Mol Microbiol 1993: 9: 1239-46.

Guatelli J, Whitfield K. Kwoh D. Barringer K. Richman D. Gengeras T. Isothermal, in vitro amplification of nucleic acids by a multienzyme reaction modeled after retroviral replication. Proc Natl Acad Sci USA 1990: 87: 1874-1878.

Guerrero et al. Evaluation of the rpoB gene in rifampicin susceptible and resistant *M. avium* and *M. intracellulare*. J. Antimicrob. Chemotherapy 1994: 33: 661-663.

Heifets L. Qualitative and quantitative drug-susceptibility tests in mycobacteriology. Pulmonary perspective. Am Rev Respir Dis 1988: 137: 1217-1227.

Honore N. and Cole S. Molecular basis of rifampicin resistance in *M. leprae*. Antimicrobial Agents and Chemotherapy 1993: 37: 414-418.

Kapur V. Li L. Iordanescu S. et al. Characterization by automated DNA sequencing of mutations in the genie (rpoB) encoding the RNA polymerase β subunit in rifampicin resistant *Mycobacterium tuberculosis* strains from New York City and Texas. J. Clin. Microbiol. 1994: 32: 1095-1098.

Kwoh D. Davis G. Whitfield K. Chappelle H. Dimichele L. Gingeras T. Transcription-based amplification system and detection of amplified human immunodeficiency virus type 1 with a bead-based sandwich hybridization format. Proc Natl Acad Sci USA 1989: 86: 1173-1177.

Kwok S. Kellogg D. McKinney N. Spasic D. Goda L. Levenson C. Sinisky J. Effects of primer-template mismatches on the polymerase chain reaction: Human immunodeficiency views type 1 model studies. Nucl. Acids Res. 1990; 18: 999.

Landgren U. Kaiser R. Sanders J. Hood L. A ligase-mediated gene detection technique. Science 1988: 241: 1077-1080.

Lomeli H. Tyagi S. Printchard C. Lisardi P. Kramer F. Quantitative assays based on the use of replicatable hybridization probes. Clin Chem 1989: 35: 1826-1831.

Matsukura M. Shinozuka K, Zon G. Mitsuya H. Reitz M. Cohen J. Broder S (1987) Phspliorothioate analogs of oligodeoxynucleotides: inhibitors of replication and cytopathic effects of human immunodeficiency virus. Proc. Natl. Acad. Sci. USA 84(21):7706-10.

Middlebrook G. (1954a). Isoniazid-resistance and catalase activity of tubercle bacilli. Am. Rev. Tuberc., 69: 471-472.

Middlebrook G., Cohn M. L., Schaefer W. B. (1954b). Studies on isoniazid and tubercle bacilli. III. The isolation, drug-susceptibility, and catalase-testing of tubercle bacilli from isoniazid-treated patients. Am. Rev. Tuberc., 70: 852-872.

Miller P, Yano J. Yano E. Carroll C. Jayaram K. Ts'o P (1979) Nonionic nucleic acid analogues. Synthesis and characterization of dideoxyribonucleoside methylphosphonates. Biochemistry 18(23):5134-43.

Nair J. Rouse D A, Bai G H, Morris S L. The rpsL gene and streptomycine resistance in single and multiple drug-resistant strains or *Mycobacterium tuberculosis*. Mol. Microbiol. 1993: 10: 521-527.

Nielsen P. Egholm M, Berg R, Buchardt O (1991) Sequence-selective recognition of DNA by strand displacement with a thymine-substituted polyamide. Science 254 (5037): 1497-500.

Nielsen P, Egholm M. Berg R. Buchardt O (1993) Sequence specific inhibition of DNA restriction enzyme cleavage by PNA. Nucleic-Acids-Res. 21(2):197-200.

Saiki R, Walsh P, Levenson C. Erlich H. Genetic analysis of amplified DNA with immobilized sequence-specific oligonucleotide probes Proc Natl Acad Sci USA 1989: 86:6230-6234.

Stoeckle M Y, Guan L. Riegler N et al. Catalase-peroxidase gene sequences in Isoniazid-sensitive and -resistant strains of *Mycobacterium tuberculosis* from New York City. J. Inf. Dis. 1993; 168: 1063-65.

Stuyver L. Rossau R. Wyseur A. et al. Typing of hepatitis C virus isolates and characterization of new subtypes using a line probe assay. J. Gen. Virol. 1993; 74: 1093-1102.

Telenti A., Imboden P., Marchesi F. et al. Detection of rifampicin-resistance mutations in *Mycobacterium tuberculosis* Lancet 1993a; 341: 647-50.

Telenti A., Imboden P. Marchesi F. et al. Direct, automated detection of Rifampin-resistant *Mycobacterium tuberculosis* by polymerase chain reaction and simple-strand conformation polymophism analysis. Antimicrob Agents Chemother 1993b: 37: 2054-58.

Wu D, Wallace B. The ligation amplification reaction (LAR)—amplification of specific DNA sequences using sequential rounds of template-dependent ligation. Genomics 1989: 4:560-569.

Youatt J. (1969). A review of the action of isoniazid. Am. Rev. Respir. Dis. 99 729-749.

Zhang Y., Heym B. Allen B., Young D. and Cole S. The catalase-peroxidase gene and isoniazid resistance of *Mycobacterium tuberculosis*. Nature 1992: 358: 591-93.

The invention claimed is:

1. An isolated oligonucleotide selected from the group consisting of:

| | |
|---|---|
| S1, | (SEQ ID NO: 1) |
| S33, | (SEQ ID NO: 5) |
| S4, | (SEQ ID NO: 6) |
| S44, | (SEQ ID NO: 7) |
| S444, | (SEQ ID NO: 43) |
| S55, | (SEQ ID NO: 10) |
| S555, | (SEQ ID NO: 39) |
| S5555, | (SEQ ID NO: 40) |
| S6, | (SEQ ID NO: 11) |
| S66, and | (SEQ ID NO: 12) | the RNA form of said SEQ ID NOs wherein T is replaced by U, and the complementary form of said SEQ ID NOs.

2. A composition comprising at least one isolated oligonucleotide selected from the group consisting of:

| | |
|---|---|
| S1, | (SEQ ID NO: 1) |
| S33, | (SEQ ID NO: 5) |
| S4, | (SEQ ID NO: 6) |
| S44, | (SEQ ID NO: 7) |
| S444, | (SEQ ID NO: 43) |
| S55, | (SEQ ID NO: 10) |
| S555, | (SEQ ID NO: 39) |
| S5555, | (SEQ ID NO: 40) |
| S6, | (SEQ ID NO: 11) |
| S66, and | (SEQ ID NO: 12) | the RNA form of said SEQ ID NOs wherein T is replaced by U, and the complementary form of said SEQ ID NOs.

3. A kit for the detection of the resistance to rifampicin of *Mycobacterium tuberculosis* present in a biological sample comprising the following components:

(i) at least one rpoB gene fragment selected from the group consisting of:

| | |
|---|---|
| S1, | (SEQ ID NO: 1) |
| S33, | (SEQ ID NO: 5) |
| S4, | (SEQ ID NO: 6) |
| S44, | (SEQ ID NO: 7) |
| S444, | (SEQ ID NO: 43) |
| S55, | (SEQ ID NO: 10) |
| S555, | (SEQ ID NO: 39) |
| S5555, | (SEQ ID NO: 40) |
| S6, | (SEQ ID NO: 11) |
| S66, and | (SEQ ID NO: 12) | the RNA form of said SEQ ID NOs wherein T is replaced by U, and the complementary form of said SEQ ID NOs;

(ii) a hybridization buffer, or components necessary for producing said buffer; and (iii) a wash solution, or components necessary for producing said solution.

4. The kit according to claim 3, further enabling *Mycobacterium* species determination, and further comprising at least one isolated oligonucleotide selected from the group consisting of:

| | |
|---|---|
| MT-POL-2, | (SEQ ID NO: 24) |
| MT-POL-3, | (SEQ ID NO: 25) |
| MT-POL-4, | (SEQ ID NO: 26) |
| MT-POL-5, | (SEQ ID NO: 27) |
| MP-POL-1, | (SEQ ID NO: 28) |
| MA-POL-1, | (SEQ ID NO: 29) |
| MS-POL-1, | (SEQ ID NO: 38) |
| MK-POL-1, | (SEQ ID NO: 55) |
| MI-POL-1, | (SEQ ID NO: 68) |
| ML-POL-1, and | (SEQ ID NO: 57) | the RNA form of said SEQ ID NOs wherein T is replaced by U, and the complementary form of said SEQ ID NOs.

5. The kit according to claim 3, for the simultaneous detection of *M. tuberculosis* and its resistance to rifampicin, wherein (i) said rpoB gene fragment of component (i) is selected from the group of consisting of:

| | |
|---|---|
| S1, | (SEQ ID NO: 1) |
| S33, | (SEQ ID NO: 5) |
| S4, | (SEQ ID NO: 6) |
| S44, | (SEQ ID NO: 7) |
| S444, | (SEQ ID NO: 43) |
| S55, | (SEQ ID NO: 10) |
| S555, | (SEQ ID NO: 39) |
| S5555, | (SEQ ID NO: 40) |
| S6, | (SEQ ID NO: 11) |
| S66, and | (SEQ ID NO: 12) | the RNA form of said SEQ ID NOs wherein T is replaced by U, and the complementary form of said SEQ ID NOs; and wherein (ii) said kit further comprises at least one additional rpoB gene fragment selected from the group consisting of:

| | |
|---|---|
| MT-POL-2, | (SEQ ID NO: 24) |
| MT-POL-3, | (SEQ ID NO: 25) |
| MT-POL-4, | (SEQ ID NO: 26) |
| MT-POL-5, and | (SEQ ID NO: 27) | the RNA form of said SEQ ID NOs wherein T is replaced by U, and the complementary form of said SEQ ID NOs.

6. A method for the identification of a mycobacterial species and the simultaneous detection of its resistance to rifampicin, comprising (i) optionally releasing, isolating or concentrating the polynucleotides present in the sample;

(ii) optionally amplifying the relevant part of the rpoB gene with at least one suitable primer pair;

(iii) simultaneously hybridizing the polynucleotides of steps (i) or (ii) with at least two rpoB gene fragments, wherein the first rpoB gene fragment is selected from the group consisting of:

| | |
|---|---|
| S1, | (SEQ ID NO: 1) |
| S33, | (SEQ ID NO: 5) |
| S4, | (SEQ ID NO: 6) |
| S44, | (SEQ ID NO: 7) |
| S444, | (SEQ ID NO: 43) |
| S55, | (SEQ ID NO: 10) |
| S555, | (SEQ ID NO: 39) |
| S5555, | (SEQ ID NO: 40) |

-continued

| | |
|---|---|
| S6, | (SEQ ID NO: 11) |
| S66, and | (SEQ ID NO: 12) | the RNA form of said SEQ ID NOs wherein T is replaced by U, and the complementary form of said SEQ ID NOs;

and wherein the second rpoB gene fragment is selected from the group consisting of:

| | |
|---|---|
| MT-POL-2, | (SEQ ID NO: 24) |
| MT-POL-3, | (SEQ ID NO: 25) |
| MT-POL-4, | (SEQ ID NO: 26) |
| MT-POL-5, | (SEQ ID NO: 27) |
| MP-POL-1, | (SEQ ID NO: 28) |
| MA-POL-1, | (SEQ ID NO: 29) |
| MS-POL-1, | (SEQ ID NO: 38) |
| MK-POL-1, | (SEQ ID NO: 55) |
| MI-POL-1, | (SEQ ID NO: 68) |
| ML-POL-1, | (SEQ ID NO: 57) |
| ML-S1, | (SEQ ID NO: 58) |
| ML-S2, | (SEQ ID NO: 59) |
| ML-S3, | (SEQ ID NO: 60) |
| ML-S4, | (SEQ ID NO: 61) |
| ML-S5, | (SEQ ID NO: 62) |
| ML-S6, and | (SEQ ID NO: 63) | the RNA form of said SEQ ID NOs wherein T is replaced by U, and the complementary form of said SEQ ID NOs;

(iv) detecting the hybrids formed in step (iii); and (v) inferring the identification of a mycobacterial species and its resistance to rifampicin from the differential hybridization signal(s) obtained in step (iv).

7. The kit according to claim 3, wherein said at least one rpoB gene fragment is an S-probe.

* * * * *